United States Patent
Li et al.

(10) Patent No.: US 9,732,055 B2
(45) Date of Patent: *Aug. 15, 2017

(54) COMPOSITIONS AND METHODS FOR CANCER TREATMENT

(75) Inventors: Chiang Jia Li, Cambridge, MA (US); Keith Mikule, Norwood, MA (US); Youzhi Li, Westwood, MA (US)

(73) Assignee: Boston Biomedical, Inc., Cambridge, MA (US)

( * ) Notice: Subject to any disclaimer, the term of this patent is extended or adjusted under 35 U.S.C. 154(b) by 505 days.

This patent is subject to a terminal disclaimer.

(21) Appl. No.: 12/677,516

(22) PCT Filed: Sep. 10, 2008

(86) PCT No.: PCT/US2008/075906
§ 371 (c)(1),
(2), (4) Date: Aug. 12, 2010

(87) PCT Pub. No.: WO2009/036101
PCT Pub. Date: Mar. 19, 2009

(65) Prior Publication Data
US 2010/0310503 A1 Dec. 9, 2010

Related U.S. Application Data

(60) Provisional application No. 60/971,144, filed on Sep. 10, 2007, provisional application No. 61/013,372, filed on Dec. 13, 2007.

(51) Int. Cl.
*A61K 31/33* (2006.01)
*C07D 307/92* (2006.01)
*A61K 31/38* (2006.01)
*C07D 333/74* (2006.01)

(52) U.S. Cl.
CPC ............ *C07D 307/92* (2013.01); *A61K 31/38* (2013.01); *C07D 333/74* (2013.01)

(58) Field of Classification Search
None
See application file for complete search history.

(56) References Cited

U.S. PATENT DOCUMENTS

| | | | |
|---|---|---|---|
| 6,337,346 B1 | 1/2002 | Lee et al. | |
| 7,019,147 B1 * | 3/2006 | Barth et al. | 548/125 |
| 7,538,234 B2 | 5/2009 | Iida et al. | |
| 7,910,752 B2 | 3/2011 | Tokuda et al. | |
| 2004/0006009 A1 | 1/2004 | Larsen | |
| 2004/0092428 A1 | 5/2004 | Chen et al. | |
| 2004/0138189 A1 | 7/2004 | Sebti et al. | |
| 2005/0010060 A1 | 1/2005 | Blokhin et al. | |
| 2005/0049207 A1 | 3/2005 | Kaufmann et al. | |
| 2006/0019256 A1 | 1/2006 | Clarke et al. | |
| 2006/0099251 A1 | 5/2006 | Johannsson | |
| 2006/0222696 A1 | 10/2006 | Okada et al. | |
| 2006/0247318 A1 | 11/2006 | Song et al. | |
| 2006/0252674 A1 | 11/2006 | Peritt et al. | |
| 2006/0279011 A1 | 12/2006 | Palakodaty et al. | |
| 2007/0060521 A1 | 3/2007 | Jove et al. | |
| 2007/0123502 A1 | 5/2007 | Turkson et al. | |
| 2007/0238770 A1 | 10/2007 | Gougoutas et al. | |
| 2009/0042977 A1 | 2/2009 | Tokuda et al. | |

FOREIGN PATENT DOCUMENTS

| | | |
|---|---|---|
| CA | 2017806 A1 | 4/1994 |
| EP | 1134216 B1 | 4/2001 |
| JP | 04139177 A | 5/1992 |
| JP | H11021284 A1 | 1/1999 |
| JP | 2004224802 * | 8/2004 |
| WO | WO9962909 A2 | 12/1999 |
| WO | WO-0044774 A2 | 8/2000 |
| WO | WO-2004026253 A2 | 4/2004 |
| WO | WO2004046120 A2 | 6/2004 |
| WO | WO-2005033048 A2 | 4/2005 |
| WO | WO-2005058829 A1 | 6/2005 |
| WO | WO-2005110477 A2 | 11/2005 |
| WO | WO-2006056399 A2 | 6/2006 |
| WO | WO 2006091837 A2 * | 8/2006 |
| WO | WO2006098355 A1 | 9/2006 |
| WO | WO-2006113790 A2 | 10/2006 |
| WO | WO-2007100640 A2 | 9/2007 |
| WO | WO-2007115269 A2 | 10/2007 |
| WO | WO-2008077062 A2 | 6/2008 |
| WO | WO-2008094321 A2 | 8/2008 |
| WO | WO2008094321 A2 | 8/2008 |

OTHER PUBLICATIONS

Paridaens et al., "Paclitaxel versus doxorubicin as first-line single-agent Chemotherapy for Metastatic Breast Cancer: a European Organization for Research and Treatment of Cancer Randomized Study with Cross-Over," J. Clin. Oncol. Feb. 2000; 18(4):724-33.*
Masayuka et al., "Cytotoxic Activity toward KB Cells of 2-Substituted Naphtho[2,3-b]furan-4,9-diones and Their Related Compounds," Biosci. Biotechnol. Biochem., 70(4), 1009-1012, (2006).*
Qiuwen et al. "Evaluation of the Potential Cancer Chemotherapeutic Efficacy of Natural Product Isolates Employing in Vivo Hollow Fiber Tests," J. Nat. Prod. 2002, 65, 842-850.*
Muller et al (J Nat Prod 62:1134-1136, 1999).*
Faloppi et al (Scientific Reports 6:24136, 2016).*
Koyoma et al. "Micellar Electrokinetic Chromatography (MEKC) Separation of Furanonaphthoquinones from Tabebuia impetiginosa" Chem. Pharm. Bull. (Tokyo), Jun. 2000, 48(6) 873-875.
Solorzano et al. "Decreased glycolytic metabolism accelerates apoptosis in response to 2-acetyl furanonaphthoquinone in K1735 melanoma irrespective of bcl-2 overexpression" Cancer Biol. Ther. (Mar. 2005) vol. 4, No. 3, pp. 329-335. [Abstract provided].

(Continued)

*Primary Examiner* — Craig Ricci

(74) *Attorney, Agent, or Firm* — Finnegan, Henderson, Farabow, Garrett & Dunner LLP

(57) ABSTRACT

The present invention relates to the composition and methods of use of Stat3 pathway inhibitors or cancer stem cell inhibitors in combination treatment of cancer.

91 Claims, 15 Drawing Sheets

(56) References Cited

OTHER PUBLICATIONS

Colman et al. "Effect of a Small Molecule Inhibitor of the JAK2/STAT3 Pathway on Self-Renewal of Gliobastoma Stem Cells." *J. Clin. Oncol.* 26.15S(2008). (Abstract Only).
Desmond et al. "The Synthetic Furanonaphthoquinone Induces Growth Arrest, Apoptosis and Differentiation in a Variety of Leukaemias and Multiple Myeloma Cells." *Brit. J. Haematol.* 131.4(2005):520-529.
Frank. "STAT3 as a Central Mediator of Neoplastic Cellular Transformations." *Cancer Lett.* 251.2(2007):199-210.
Johnson et al "Abrogation of Signal Transducer and Activator of Transcription 3 Reactivation After Src Kinase Inhibition Results in Synergistic Antitumor Effects." *Clin. Cancer Res.* 13.14(2007):4233-4244.
Katoh et al. "STAT3-Induced WNT5A Signaling Loop in Embryonic Stem Cells, Adult Normal Tissues, Chronic Persistent Inflammation, Rheumatoid Arthritis and Cancer." *Int. J. Mol. Med.* 19.2(2007):273-278.
Kim et al. "Inhibition of Signal Transducer and Activator of Transcription 3 Activity Results in Down-Regulation of Survivin Following Irradiation." *Mol. Cancer Thera.* 5.11(2006):2659-2665.
Sun et al. "Comparison of Effects of the Tyrosine Kinase Inhibitors AG957, AG490, and STI571 on BCR-ABL-Expressing Cells, Demonstrating Synergy Between AG490 and STI571." *Blood.* 97.7(2001):2008-2015.
Yao et al. "Experimental Study on the Growth Inhibition of Bladder Cancer Cells by Signal Conduction Blocker AG490." *J. Clin. Urol.* 21.5(2006):379-382. (English Abstract).
Yau et al. "Inhibition of Integrin-Linked Kinase by QLT0254 Inhibits Akt-Dependent Pathways and is Growth Inhibitory in Orthotopic Primary Pancreatic Cancer Xenografts." *Cancer Res.* 65.4(2005):1497-1504.
Zhou et al. "Activation of the PTEN/mTOR/STAT3 Pathway in Breast Cancer Stem-Like Cells is Required for Viability and Maintenance." *PNAS.* 104.41(2007):16158-16163.
Zhou et al. "Corrections: Activation of the PTEN/mTOR/STAT3 Pathway in Breast Cancer Stem-Like Cells is Required for Viability and Maintenance." *PNAS.* 104.49(2007).
Johnston et al. "STAT3 Signaling: Anticancer Strategies and Challenges." *Mol. Interv.* 11.1(2011):18-26.
STN Accession No. 1986 568912.
STN Accession No. 1992:245248.
STN Accession No. 1999:157137.
STN Accession No. 2002:33229.
Ailles and Weissman "Cancer stem cells in solid tumors," Curr Opin Biotechnol, 18(5):460-6 (2007).
Al-Hajj "Therapeutic implications of cancer stem cells," Curr Opin Genet Dev, 14(1):43-7(2004).
Alvi "Functional and molecular characterization of mammary side population cells," Breast Cancer Res, 5(1): R1-8 (2003).
Anderson "The process of structure-based drug design" Chem and Biol 10:787-797, 2003.
Arany "Correlation between pretreatment levels of interferon response genes and clinical responses to an immune response modifier (Imiquimod) in genital warts," Antimicrob Agents Chemother, 44(7):1869-73(2000).
Benkhart "Role of Stat3 in lipopolysaccharide-induced IL-10 gene expression," J Immunol, 165(3):1612-7 (2000).
Bonnet "Normal and leukaemic stem cells," Br J Haematol, 130(4):469-79 (2005).
Bonnet and Dick "Human acute myeloid leukemia is organized as a hierarchy that originates from a primitive hematopoietic cell," Nat Med, 3(7):730-7 (1997).
Braatz "Crystallization: Particle Size Control." Encyclopedia of Pharmaceutical Technology. Swarbrick, ed. New York: Informa Healthcare. Third Edition (2007):858-871.
Bromberg "Stat3 as an oncogene," Cell, 98(3):295-303(1999).
Burdelya "Stat3 activity in melanoma cells affects migration of immune effector cells and nitric oxide-mediated antitumor effects," J Immunol, 174(7):3925-31(2005).

Byrn Solid-State Chemistry of Drugs, 2d, Chapter 11 hydrates and solvates/hydrates, 233-247.
Campbell "Cytokine-mediated inflammation, tumorigenesis, and disease associated JAKISTAT/SOCS signaling aircuits in the CNS," Brain Res Brain Res Rev, 48(2):166-77(2005).
Carson "Interferon-alpha-induced activation of signal transducer and activator of transcription proteins in malignant melanoma," Clin Cancer Res, 4(9):2219-28(1998).
Cesari "Inflammatory markers and onset of cardiovascular events: results from the Health ABC study," Circulation, 108(19):2317-22(2003).
Caira, Crystalline Polymorphism of Oeganic Compounds, Topics in Chemistry, vol. 198 (1998).
Clarke "Cancer Stem Cells—Perspectives on Current Status and Future Directions: AACR Workshop on Cancer Stem Cells." Cancer Research. 66.19(2006):9339-9344.
Collins , "Prospective identification of tumorigenic prostate cancer stem cells," Cancer Res, 65(23):10946-51 (2005).
Dalerba "Phenotypic characterization of human colorectal cancer stem cells," Proc Natl Acad Sci USA, 104(24):10158-63(2007).
Dien et al., "Signal transducers and activators of Transcription-3 up-regulates tissue inhibitor of metalloproteinase-1 expression and decreases invasiveness of breast cancer" Am. J. Pathol. (2006) 169 (2) 633-642.
Doyle and Ross "Multidrug resistance mediated by the breast cancer resistance protein BCRP (ABCG2)," Oncogene, 22(47):7340-58 (2003).
Fagerholm "Experimental Estimation of the Effective Unstirred Water Layer Thickness in the Human Jejunum, and its Importance in Oral Drug Absorption." Eur. J. Pharm. 3(1995):247-253.
Fotsing "Identification of an Anti-Inflammatory Principle from the Stem Bark of Millettia versicolor", Planta Med, Aug. 1, 2003 (Aug. 1, 2013), pp. 767-770, XP55274254, Germany.
Frank "ABCB5-mediated doxorubicin transport and chemoresistance in human malignant melanoma," Cancer Res, 65(10):4320-33 (2005).
Fu, "STAT3 in immune responses and inflammatory bowel disease," Cell Res, 16(2):214-9(2006).
Gafner "Antifungal and Antibacterial Naphthoquinones from Newbouldia laevis Roots." Phytochemistry. 42.5(1996):1315-1320.
Goodall "Isolation and Functional Properties of Murine Hematopoietic Stem Cells That are Replicating In Vivo." J. Exp. Med. 183.4(1996)1797-1806.
Gormann "Furanonaphthoquinones, atraric acid and a benzofuran from the stem barks of Newbouldia laevis." Phytochemistry. 64.2(2004):583-587.
Haleblian "Pharmaceutical Applications of Polymorphism" J. Pharm. Sci. Aug. 1969, p. 911.
Hambardzumyan "Radiation resistance and stem-like cells in brain tumors," Cancer Cell, 10(6):454-6 (2006).
Han Li., "Unusual Naphthoquinone Derivatives from the Twigs of Avicennia marina " J. Nat. Prod. 2007, 70, 923-927.
Haraguchi "Characterization of a Side Population of Cancer Cells From Human Gastrointestinal System." Stem Cells. 24.3(2006):506-513.
Harris "Cutting edge: An in vivo requirements for STAT3 signaling in TH17 development and TH17-dependent autoimmunity," J Immunol, 179(7):4313-7(2007).
Hirai "Furanonaphthoquinone Analogs Possessing Preferential Antitumor Activity Compared to Normal Cells." Cancer Detection and Prevention. 23.6(1999):539-550.
Ho "Side population in human lung cancer cell lines and tumors is enriched with stem-like cancer cells," Cancer Res., 67(10):4827-33 (2007).
Ishihara and Hirano "IL-6 in autoimmune disease and chronic inflammatory proliferative disease," Cytokine Growth Factor Rev, 13(4-5):357-68(2002).
Itoigawa "Cancer chemopreventive activity of naphthoquinones and their analogs from Avicennia plants." Cancer Letters. 174. 2(2001):135-139.
Ivashkiv and Tassiulas "Can SOCS make arthritis better?", J Clin Invest, 111(6):795-7(2003).

(56) References Cited

OTHER PUBLICATIONS

Jones "Cancer stem cells: are we missing the target?," J Natl Cancer Inst, 96(8):583-5 (2004).
Kim, "JAK-STAT signaling mediates gangliosides-induced inflammatory responses in brain microglial cells," J Biol Chem, 277(43):40594-601(2002).
Kondo, "Persistence of a small subpopulation of cancer stem-like cells in the C6 glioma cell line," Proc Natl Acad Sci USA, 101(3):781-6 (2004).
Koyanagi "A Facile Synthesis of 2-Acteylnaphtho[2,3-b]furan-4,9-dione," Journal of Heterocyclic Chemistry, (1995), vol. 32, pp. 1289-1291.
Koyanagi "A New Synthetic of 2-Substituted Naphtho[2,3-b]furan-4,9-dione," Journal of Heterocyclic Chemistry, (1997), vol. 34, pp. 407-412.
Krause "Rheumatoid arthritis synoviocyte survival is dependent on Stat3," J Immunol, 169(11):6610-6(2002).
Lai, "Signal transducer and activator of transcription-3 activation contributes to high tissue inhibitor of metalloproteinase-1 expression in anaplastic lymphoma kinase-positive anaplastic large cell lymphoma," Am J Pathol, 164(6):2251-8(2004).
Lande "The Relationship Between Membrane Fluidity and Permeabilities to Water, Solutes, Ammonia, and Protons." J. Gen. Physiol. 106(1995):67-84.
Lee "Efficient Synthesis of Cytotoxic Furonaphthoquinone Natural Products," Synthetic Communications, 31(3), 381-386 (2001).
Li, "Identification of pancreatic cancer stem cells," Cancer Res, 67(3):1030-7(2007).
Libby, Ridker, and Maser, "Inflammation and atherosclerosis," Circulation, 105(9):1135-43(2002).
Lim, "Stat3 contributes to keloid pathogenesis via promoting collagen production, cell proliferation and migration," Oncogene, 25(39):5416-25(2006).
Ling "Mesenchymal Stem Cells Overexpressing IFN-Inhibit Breast Cancer Growth and Metastases through Stat3 Signaling in a Syngeneic Tumor Model," Cancer Microenviron, Mar. 19, 2010; 3 (I):83-95.
Lipinski "Experimental and Computational Approaches to Estimate Solubility and Permeability in Drug Discovery and Development Settings." Adv. Drug Deliv. Rev. 46.1-3(2001):3-26.
Lopes "Efficient Synthesis of Cytotoxic Quinones: 2-Acetyl-4H,9H-naphtho[2,3-b]furan-4,9-dione (6) and (±)-2-(1-Hydroxyethyl)-4H,9H-naphtho[2,3-b]furan-4,9-dione (7)," Journal of Heterocyclic Chemistry, (1984), vol. 21, pp. 621-622.
Lovato, "Constitutive STAT3 activation in intestinal T cells from patients with Crohn's disease," J Biol Chem, 278(19):16777-81(2003).
Ma "Identification and Characteristic of Tumorigenic Liver Cancer Stem/Progenitor Cells." Gastroenterology. 132.7(2007):2542-2556.
Manolagas, "Role of cytokines in bone resorption," Bone, 17(2 Suppl):63S-67S(1995).
Morrissette "High-throughput crystallization: polymorphs, salts, co-crystals and solvates of pharmaceutical solids" Adv. Drug Delivery Rev. 2004, 56, 275-300.
Ogawa "Cytotoxic Activity Toward KB Cells of 2-Substituted Naphtho[2,3-b]furan-4,9-diones and Their Related Compounds." Biosci. Biotechnol. Biochem. 70.4(2006):1009-1012.
Orshal and Khalil, "Interleukin-6 impairs endothelium-dependent NO-cGMP-mediated relaxation and enhances contraction in systemic vessels of pregnant rats," Am J Physiol Regul Integr Comp Physiol, 286(6):1013-23(2004).
Peraza-Sanchez "Cytotoxic Constituents of the Roots of Ekmanianthe longiflora," American Chemical Society Publication—Journal of Natural Products, (2000), vol. 63, pp. 492-495.
Pereira et al., "Invasion-associated MMP-2 and MMP-9 are up-regulated intracellularly in concert with apoptosis linked to melanoma cell detachment," Clinical and Experimental Metastasis (2005) 22:285-295.
Ponti, "Isolation and in vitro propagation of tumorigenic breast cancer cells with stem/progenitor cell properties," Cancer Res, 65(13):5506-11(2005).
Prince, "Identification of a subpopulation of cells with cancer stem cell properties in head and neck squamous cell carcinoma," Proc Natl Acad Sci USA, 132(7):2542-56(2007).
Puthier, Bataille, and Amiot, "IL-6 up-regulates mcl-1in human myeloma cells through JAK/STAT rather than ras/MAP kinase pathway," Eur J Immunol, 29(12):3945-50(1999).
Rao and Kingston, "Plant anticancer agents. XII. isolation and structure elucidation of new cytotoxic quinones from Tabebuia cassinoides," Journal of Natural Products, 45(5):600-604 (1982).
Ricci-Vitiani "Identification and Expansion of Human Colon-Cancer-Initiating Cells." Nature. 445.7123(2007):111-115.
Roder, "STAT3 is constitutively active in some patients with Polycythemia rubra vera," Exp Hematol, 29 (6):694-702(2001).
Schatton "Identification of Cells Initiating Human Melanomas." Nature. 451.7176(2008):345-349.
Schlette, "Survivin expression predicts poorer prognosis in anaplastic large-cell lymphoma," J Clin Oncol, 22(9):1682-8(2004).
Sengupta, "Activation of monocyte effector genes and STAT family transcription factors by inflammatory synovial fluid is independent of interferon gamma," J Exp Med, 181(3):1015-25(1995).
Shouda, "Induction of the cytokine signal regulator SOCS3/CIS3 as a therapeutic strategy for treating inflammatory arthritis," J Clin Invest, 108(12):1781-8(2001).
Simeone-Penney, "Airway epithelial STAT3 is required for allergic inflammation in a murine model of asthma," J Immunol, 178(10):6191-9(2007).
Singh, "Identification of a cancer stem cell in human brain tumors," Cancer Res, 63(18):5821-8(2003).
Song "A low-molecular-weight compound discovered through virtual database screening inhibits Stat3 function in breast cancer cells." Proc. Natl. Acad Sci. 102.13(2005): 4700-4705.
Song, "Activation of Stat3 by receptor tyrosine kinases and cytokines regulates survival in human non-small cell carcinoma cells," Oncogene, 22(27):4150-65(2003).
Song and Grandis, "STAT signaling in head and neck cancer," Oncogene, 19(21):2489-95(2000).
Steinert "HPLC separation and determination of naphtho[2,3-b]furan-4,9-diones and related compounds in extracts of Tabebuia avellanedae (Bignoniaceae)" J Chromato A 693:281-287, 1995.
Stelmasiak, "Interleukin-6 concentration in serum and cerebrospinal fluid in multiple sclerosis patients," Med Sci Monit, 6(6):1104-8(2000).
Stephens, "A common functional variant in the interleukin-6 gene is associated with increased body mass indexin subjects with type 2 diabetes mellitus," Mol Genet Metab, 82(2):180-6(2004).
Szotek, "Ovarian cancer side population defines cells with stem cell-like characteristics and Mullerian Inhibiting Substance responsiveness," Proc Natl Acad Sci USA, 103(30):11154-9(2006).
Tefferi, "Classification, diagnosis and management of myeloproliferative disorders in the JAK2V617F era," Hematology Am Soc Hematol Educ Program, 240-5 (2006).
Wang, "Identification of cancer stem cell-like side population cells in human nasopharyngeal carcinoma cell line," Cancer Res, 67(8):3716-24 (2007).
Weber-Nordt, "Constitutive activation of STAT proteins in primary lymphoid and myeloid leukemia cells and in Epstein-Barr virus (EBV)-related lymphoma cell lines," Blood, 88(3):809-16(1996).
Wermuth "Molecular Variations Based on Isoteric Replacements," The Practice of Medicinal Chemistry, Academic Press, 1996. pp. 203-237.
Williams "Two New Cytotoxic Naphthoquinones from Mendoncia cowanii from the Rainforest of Madagascar." Planta Medica. 72.6(2006):564-566.
Xie, "Stat3 activation regulates the expression of matrix metalloproteinase-2 and tumor invasion and metastasis," Oncogene, 23(20):3550-60(2004).
Zani "Furanonaphthoquinones from Tabebuia Ochracea," Phytochemistry, (1991), vol. 30, No. 7, pp. 2379-2381.

(56) References Cited

OTHER PUBLICATIONS

Zhang, "Intratumoral delivery and suppression of prostate tumor growth by attenuated Salmonella enterica serovar typhimurium carrying plasmid-based small interfering RNAs," Cancer Res, 67(12):5859-64(2007).
Reagan-Shaw Dose translation from animal to human studies revisited, The FASEB Journal, 2007 22, p. 659-661.
Kang A New Route to Naphtho[2,3-b]furan-4,9-diones from Thio-substituted 1,4-Naphthoquinones, J. Chem. Soc. Perkin Trans. 1 (1990).
Schaefer "Constitutive Activation of Stat3α in Brain Tumors: Localization to Tumor Endothelial Cells and Activation by the Endothelial Tyrosine Kinase Receptor (VEGFR-2)", Oncogene (2002) 21, 2058-2065.
Stout, http://nocancer.blogspot.com/2005/05/14-pau-darco.html.
Taylor, Technical Data Report for Pau D'Arco, Herbal Secrets of the Rainforest, 2nd edition (2003).
Alas et al., Clin Cancer Res. (2003) 9(1):316-26.
Alvarez et al., Cancer Biology & Therapy (2004) 3(11):1045-1050.
Alvarez et al., Cancer Res. (2005) 15; 65(12):5054-62.
Amin et al, Oncogene (2004) 23, 5426-5434.
Achcar et al., Arch Pathol Lab Med. (2007) 131(9):1350-60.
Aoki et al., Blood (2003) 101:1535-1542.
Barton et al., Mol Cancer Ther. (2004) 3(1):11-20.
Benekli et al., Blood (2002) 99:252-257.
Berishaj et al., Breast Cancer Res. (2007) 9(3): R32.
Biaskovich et al., Cancer Res (2003) 63: 1270-1279.
Bromberg, J., J Clin Invest (2002) 109(9) 1139-1142.
Buettner et al., Clinical Cancer Research (2002) 8(4): 945-954.
Burke et al., Oncogene. (2001) 29;20(55):7925-34.
Catlett-Falcone et al. Immunity (1999) 10(1): 105-115.
Chan et al., J. Clin. Invest. (2004) 114: 720-728.
Chang et al., J Pathol (2006) 210:224-33.
Chen et al., BMC Cancer (2007) 7:111.
Chen et al., Br J Cancer. (2007) 26;96(4):591-9.
Cho-Vega et al., Leukemia (2004) 18, 1872-1878.
Corvinus et al., Neoplasia (2005) 7, 545-555.
de Araújo et al., Oral Oncol. May 2008;44(5):439-45. (Epub: Sep. 7, 2007).
Diaz et al., Clin Cancer Research (2006) 1;12(1):20-8.
Epling-Burnette et al., J. Clin. Invest. (2001) 107:351-362.
Frank, D.A., Cancer Letters (2007) 251(2) 199-210.
Gao et al., Acta Pharmacol Sin. (2005) 26(3):377-83.
Gao et al., Acta Pharmacol Sin. (2006) 27(3):347-52.
Gao et al., FEBS Letters (2001) 488 179-184.
Garcia et al., Cell Growth Differ (1997) 8(12):1267-1276.
Garcia et al., Oncogene (2001) 20(20): 2499-2513.
Grandis et al., Oncogene (2000) 15;19(21): 2489-95.
Gritsko et al. Clinical Cancer Research (2006) 12(1): 11-19.
Haura et al., Clin Cancer Res (2005) 11(23) 8288-94.
Holtick et al., Leukemia. (2005) 19 (6):936-44.
Horiguchl et al., The Journal of Urology (2002) 168(2):762-765.
Hsiao et al., Br J Cancer. (2003) 21;89(2):344-9.
Huang et al., Gynecol Oncol. (2000) 79(1):67-73.
Itoh et al., Oncogene (2006) 25, 1195-1204.
Iwamaru et al., Oncogene (2007) 26, 2435-2444.
Kanda et al., Oncogene (2004) 23, 4921-4929.
Kijima et al., Cell Growth Diff. (2002) 13: 355-362.
Konnikova et al., BMC Cancer (2003) 3:23.
Kusaba et al., Journal of Clinical Pathology (2005) 58(8) 833-838.
Lassmann et al., J Clin Pathol. Feb. 2007;60(2):173-9.
Lai et al., J Pathol. (2006) 208(5):624-32.
Lau et al., Cancer Biol Ther. (2007) 6(12):1900-7. Epub Sep. 1, 2007.
Leong et al., Proc Natl Acad Sci USA (2003) 1;100(7):4138-43.
Li et al., Clin Cancer Res. (2006) 1;12(23):7140-8.
Li et al., J. Biol. Chem. (2002) 277, 17397-17405.
Lin et al., Am J Pathol (2005) 167:969-980.
Lin et al., J. Derm. Sci. (2007) 48(1) 64-66.
Lin et al., J. Derm. Sci. (2007) 48(1) 71-73.
Ma et al., World J Gastroent.(2004) 10(11): 1569-1573.
Masuda et al., Cancer Res. (2002) 62: 3351-3355.
Mizoguchi et al., Journal of Neuropathology and Experimental Neurology (2006) 65(12)1181-1188.
Mora et al., Cancer Res (2002) 62(22): 6659-6666.
Nielsen et al., Leukemia. (1999) 13(5):735-8.
Ning et al., Blood (2001) 97:3559-3567.
Niu et al., Cancer Res. (1999) 15;59(20):5059-63.
Niu et al., Oncogene (2002) 21(46):7001-10.
Niu et al., Oncogene (2002) 21, 2000-2008.
Pedranzini et al., J. Clin. Invest. (2004) 114:619-622.
Penjabi et al., Journal of Virology (2007) 81, 5: 2449-2458.
Qiu et al., Cancer Sci. (2007) 98(7):1099-106. Epub Apr. 23, 2007.
Rahaman et al., Oncogene (2002) 21 55:8404-8413.
Rawat et al., Blood. (2000) 15; 96(10):3514-21.
Rosen et al., Cancer (2006) 107(11) 2730-40.
Savarese et al., Cytokine (2002) 17, No. 6, pp. 324-334.
Schaeffer et al., Oncogene (2002) 21, 2058-2065.
Scheper et al., Neoplasia (2007) 9(3): 192-199.
Scholz et al., Gastroenterology (2003) 125:891-905.
Silver et al., Cancer Res. (2004) 15;64(10):3550-8.
Sommer et al., Leukemia (2004) 18, 1288-1295.
Song et al., Oncogene (2003) 22(27) 4150-65.
Spiekermann et al., Eur J Haematol (2001) 67: 63-71.
Toyonaga et al., Cancer Lett. (2003) 10;201(1):107-16.
Trovato et al., Histol Histopathol (2003) 18: 393-399.
Tsareva et al., Neoplasia (2007) 9, 4: 279-291.
Wang et al., J. Clin. Oncol. (2006) 3: 392-399.
Watson & Miller, British Journal of Cancer (1995) 71(4): 840-844.
Wei et al., Oncogene (2003) 22(3): 319-329.
Xie et al., Cancer Res. (2006) 15; 66(6):3188-96.
Yakata et al., Int J Oncol. (2007) 30(2):437-42.
Yu, H., Jove, R., Nat Rev Cancer (2004) 4(2) 97-105.

\* cited by examiner

A.

EMSA

B.

Western Blotting

(-) Verapamil

(+) Verapamil

COMPOSITIONS AND METHODS FOR CANCER TREATMENT

REFERENCE TO RELATED APPLICATIONS

This application claims priority to and the benefit of U.S. provisional patent application Nos. 60/971,144 and 61/013,372, respectively filed on Sep. 10, 2007 and Dec. 13, 2007, the entire contents of which applications are incorporated herein by reference.

FIELD OF THE INVENTION

The present invention relates to the composition and methods of use of Stat3 pathway inhibitors and cancer stem cell inhibitors in combinatorial treatment of cancers and other disorders.

BACKGROUND OF THE INVENTION

Cancer Stem Cells (CSCs)

In recent years, a new model of tumorigenesis has gained wide acceptance, where it is hypothesized that only a small fraction of the entire tumor mass are responsible for the tumorigenic activities within the tumor, whereas the old or clonal genetic model posits that all the mutated tumor cells contribute equally to such tumorigenic activities. This small fraction of tumorigenic cells, according to the new model, are transformed cells with stem-cell-like qualities and are called "cancer stem cells" (CSCs). Bonnet and Dick first demonstrated, in vivo, the presence of CSCs in acute myeloid leukemia (AML) during the 1990s. Their data showed that only a small subpopulation of human AML cells had the ability to transfer AML when transplanted into immunodeficient mice while other AML cells were incapable of inducing leukemia. Later, these CSCs were shown to have the same cellular markers, $CD34^+/CD38^-$, as primitive hematopoietic stem cells [1]. Since then, researchers have found CSCs conclusively in various types of tumors including those of the brain, breast, skin, prostate, and so on.

The CSC model of tumorigenesis would explain why tens or hundreds of thousands of tumor cells need to be injected into an experimental animal in order to establish a tumor transplant. In human AML, the frequency of these cells is less than 1 in 10,000 [2]. Even though rare within a given tumor cell population, there is mounting evidence that such cells exist in almost all tumor types. However, as cancer cell lines are selected from a sub-population of cancer cells that are specifically adapted to grow in tissue cultures, the biological and functional properties of cancer cell lines can undergo dramatic changes. Therefore, not all cancer cell lines contain CSCs.

Cancer stem cells share many similar traits with normal stem cells. For example, CSCs have self-renewal capacity, namely, the ability to give rise to additional tumorigenic cancer stem cells, typically at a slower rate than other dividing tumor cells, as opposed to a limited number of divisions. CSCs also have the ability to differentiate into multiple cell types, which would explain histological evidences that not only many tumors contain multiple cell types native to the host organ, but also that heterogeneity is commonly retained in tumor metastases. CSCs have been demonstrated to be fundamentally responsible for tumorigenesis, cancer metastasis, and cancer reoccurrence. CSCs are also called tumor initiating cells, cancer stem-like cells, stem-like cancer cells, highly tumorigenic cells, tumor stem cells, solid tumor stem cells, or super malignant cells.

The existence of cancer stem cells has fundamental implications for future cancer treatments and therapies. The efficacy of current cancer treatments are, in the initial stages of testing, often measured by the size of the tumor shrinkage, i.e., the amount of tumor mass that is killed off. As CSCs would form a very small proportion of the tumor and have markedly different biologic characteristics than their more differentiated progenies, the measurement of tumor mass may not necessarily select for drugs that act specifically on the stem cells. In fact, cancer stem cells appear to be resistant to radiotherapy (XRT) and are also refractory to chemotherapeutic and targeted drugs [3-5]. Normal somatic stem cells are naturally resistant to chemotherapeutic agents—they have various pumps (such as MDR) that pump out drugs, and efficient DNA repair mechanisms. Further, they also have a slow rate of cell turnover while chemotherapeutic agents target rapidly replicating cells. Cancer stem cells, being the mutated counterparts of normal stem cells, may also have similar mechanisms that allow them to survive drug therapies and radiation treatment. In other words, conventional chemotherapies and radiotherapies kill differentiated or differentiating cells, which form the bulk of the tumor that are unable to regenerate tumors. The population of cancer stem cells that gave rise to the differentiated and differentiating cells, on the other hand, could remain untouched and cause a relapse of the disease. A further danger for the conventional anti-cancer therapy is the possibility that the treatment of, for instance, chemotherapy, leaves only chemotherapy-resistant cancer stem cells, and the ensuing recurrent tumor will likely also be resistant to chemotherapy.

Since the surviving cancer stem cells can repopulate the tumor and cause relapse, it is imperative that anti-cancer therapies include strategies against CSCs (see FIG. 1). This has been likened to the need for eliminating dandelion roots in order to prevent weed regrowth [6]. By selectively targeting cancer stem cells, it becomes possible to treat patients with aggressive, non-resectable tumors, and refractory or recurrent cancers, as well as preventing tumor metastasis and recurrence. Development of specific therapies targeting cancer stem cells therefore holds hope for survival and improved quality of life of cancer patients, especially for those with metastatic cancers. The key to unlocking this untapped potential is the identification and validation of pathways that are selectively important for cancer stem cell self-renewal and survival. Though multiple pathways underlying tumorigenesis in cancer and in embryonic stem cells or adult stem cells have been elucidated in the past, no pathways have been identified and validated for cancer stem cell self-renewal and survival.

There has also been a lot of research into the identification and isolation of cancer stem cells. Methods used mainly exploit the ability of CSCs to efflux drugs, or are based on the expression of surface markers associated with cancer stem cells.

For example, since CSCs are resistant to many chemotherapeutic agents, it is not surprising that CSCs almost ubiquitously overexpress drug efflux pumps such as ABCG2 (BCRP-1) [7-11], and other ATP binding cassette (ABC) superfamily members [12, 13]. Accordingly, the side population (SP) technique, originally used to enrich hematopoietic and leukemic stem cells, was also employed to identify and isolate CSCs [14]. This technique, first described by Goodell et al., takes advantage of differential ABC transporter-dependent efflux of fluorescent dyes such as Hoechst 33342 to define and isolate a cell population enriched in CSCs [10, 15]. Specifically, the SP is revealed by blocking drug efflux with verapamil, at which point the dyes can no longer be pumped out of the SP.

Researchers have also focused on finding specific markers that distinguish cancer stem cells from the bulk of the tumor. Most commonly expressed CSC surface markers include CD44, CD133, and CD166 [16-24]. Sorting tumor cells based primarily upon the differential expression of these surface marker(s) have accounted for the majority of the highly tumorigenic CSCs described to date. Therefore, these surface markers are well validated for the identification and isolation of cancer stem cells from cancer cell lines and from bulk tumor tissues.

Stat3 Pathway

There are many different genetic defects in mammalian or human cancer cells, and many have been studied in the quest to cure cancer. For example, the p53 tumor suppressor has been found to be defective or altogether absent in more than half of the human cancers. The STAT (Signal Transducers and Activator of Transcription) protein family are latent transcription factors activated in response to cytokines/growth factors to promote proliferation, survival, and other biological processes. Among them, Stat3 is activated by phosphorylation of a critical tyrosine residue mediated by growth factor receptor tyrosine kinases, Janus kinases, or the Src family kinases, etc. These kinases include but are not limited to EGFR, JAKs, Abl, KDR, c-Met, Src, and Her2 [25]. Upon tyrosine phosphorylation, Stat3 forms homodimers, translocates to the nucleus, binds to specific DNA-response elements in the promoter regions of the target genes, and induces gene expression [26] (see FIG. 2).

In normal cells, Stat3 activation is transient and tightly regulated, lasting from 30 minutes to several hours. However, Stat3 is found to be aberrantly active in a wide variety of human cancers, including all the major carcinomas as well as some hematologic tumors. Stat3 plays multiple roles in cancer progression. As a potent transcription regulator, it targets genes involved in many important cellular functions, such as Bcl-xl, c-Myc, cyclin D1, Vegf, MMP-2, and survivin [27-32]. It is also a key negative regulator of tumor immune surveillance and immune cell recruitment [33-35].

Ablating Stat3 signaling by antisense, siRNA, a dominant-negative form of Stat3, and/or blockade of tyrosine kinases inhibits certain cancer cell lines or tumors in vitro and/or in vivo [26, 28, 36, 37]. But no clear link between Stat3 and cancer stem cell functionality have ever been empirically made. Nor have researchers found an effective Stat3 pathway inhibitor to explore potential therapeutic uses with regard to cancers that have been found to contain cancer stem cells. As described earlier, cancer stem cells (CSCs) have been recently demonstrated to be fundamentally responsible for tumorigenesis, cancer metastasis and cancer reoccurrence, and should be taken into consideration in designing any curative therapy that targets a tumor known to have these cells no matter how small a fraction of the tumor mass they may constitute.

In diseases other than cancer, over-activation of Stat3 by various cytokines, such as interleukin 6 (IL6), has been demonstrated in a number of autoimmune and inflammatory diseases [38]. Recently, it has been revealed that the Stat3 pathway also promotes pathologic immune responses through its essential role in generating TH17 T cell responses [39]. In addition, IL6-Stat3 pathway mediated inflammation has been found to be the common causative origin for atherosclerosis, peripheral vascular disease, coronary artery disease, hypertension, osteoporosis, type 2 diabetes, and dementia.

SUMMARY

The present invention is predicated, in part, on empirical evidence provided herein that Stat3 plays a key role in both the survival and self-renewal capacity of cancer stem cells (CSCs) across a broad spectrum of cancers. The present invention also provides data that confirms certain compounds act as Stat3 pathway inhibitors and that they effectively inhibit CSCs both in vitro and in vivo.

Accordingly, a first aspect of the invention provides a method of treating a subject with a disorder that is associated with aberrant Stat3 pathway activity, the method comprising the steps of: (a) administering to the subject a first amount of a first agent to inhibit at least some of the aberrant Stat3 pathway activity; and (b) administering to the subject a second amount of a second agent comprising a signal transduction inhibitor.

The first agent may inhibit Stat3 pathway activity through at least one of the following actions: substantially inhibiting phosphorylation of the Stat3 protein, substantially inhibiting dimerization of the Stat3 protein, substantially inhibiting nuclear translocation of the Stat3 protein, substantially inhibiting DNA-binding activity of the Stat3 protein, and substantially inhibiting transcription activities of the Stat3 protein.

In one embodiment, the first agent is selected from the group consisting of 2-(1-hydroxyethyl)-naphtho[2,3-b]furan-4,9-dione, 2-Acetyl-7-Chloro-naphtho[2,3-b]furan-4,9-dione, 2-Acetyl-7-Fluoro-naphtho[2,3-b]furan-4,9-dione, 2-acetylnaphtho[2,3-b]furan-4,9-dione, 2-ethyl-naphtho[2,3-b]furan-4,9-dione, an enantiomer, diastereomer, tautomer, and a salt or solvate thereof (hereafter referred to as the "Compound of the Invention").

Non-cancer disorders that can be treated by methods of the first aspect of the invention include but are not limited to: autoimmtme diseases, inflammatory diseases, inflammatory bowel diseases, arthritis, asthma, and systemic lupus erythematosus, autoimmune demyelination disorder, Alzheimer's disease, stroke, ischernia reperfusion injury and multiple sclerosis, Cancers that can be treated by the methods include but are not limited to: breast cancer, head and neck cancer, lung cancer, ovarian cancer, pancreatic cancer, colorectal carcinoma, prostate cancer, renal cell carcinoma, melanoma, hepatocellular carcinomas, cervical cancer, sarcomas, brain tumors, gastric cancers, multiple myeloma, leukemia, lymphomas, Esophageal cancer, and dermatological cancer. These non-cancer and cancerous disorders are known to be associated with aberrant Stat3 pathway activities.

In one feature, the second agent is a targeted agent, which can be a growth factor receptor-targeting agent, a kinase-targeting agent, or an angiogenesis inhibitor.

In a second aspect, the present invention provides a method of treating a subject of a cancer that is associated with aberrant Stat3 pathway activity, the method comprising the steps of: (a) administering to the subject a first amount of a first agent to inhibit at least some of the aberrant Stat3 pathway activity; and (b) administering to the subject a second amount of a second anti-cancer agent.

While features regarding the first agent can be similar to those described with regard to the first aspect of the invention, the second anti-cancer agent can be a cytotoxic agent, or a chemotherapeutic agent. In one embodiment, the second agent is a standard first-line treatment for at least one cancer.

In one feature, the anti-cancer agent is a DNA-damaging agent, an antimitotic agent, and/or an antimetabolite agent. For example, the DNA-damaging agent can be an alkylating agent, a topoisomerase inhibitor, or a DNA intercalator. In one embodiment, the second agent is one of carboplatin, doxorubicin, gemcitabine, docetaxel, or etoposide.

Cancers that can be treated by methods of the second aspect of the invention include those known to be associated with aberrant Stat3 pathway activities, which are listed above, and not repeated here.

Since cancer stem cells are generally resistant to radiotherapy and conventional chemotherapies, a drug that targets cancer stem cells should have synergistic effect when used in combination with other anti-cancer therapies. Therefore, according to a third aspect in the present invention, a method of treating cancer in a subject includes the steps of: (a) administering to the subject a first amount of a first anti-cancer agent to inhibit a cancer stem cell (CSC) population; and (b) administering to the subject a second amount of a second anti-cancer agent to inhibit a plurality of normal cancer cells.

In various embodiments, step (a) of this method inhibits at least one CSC from self-renewal, and/or kills at least one CSC. In an embodiment, the first amount of the first anti-cancer agent also kills a plurality of normal cancer cells. In an embodiment, step (a) inhibits at least some Stat3 pathway activity in cancer stem cells. The first anti-cancer agent shares the same features and characteristics as the first agent in methods according to the first aspect of the invention, since this invention has provided evidence that Stat3 pathway inhibitors can effectively inhibit CSCs. The shared features include, for example, various steps of the Stat3 pathway that the first anti-cancer agent recited here can target. In various embodiments, the first anti-cancer agent can be a small molecule Stat3 inhibitor, an RNAi agent against Stat3, an antisense agent against Stat3, a peptidomimetic Stat3 inhibitor, or a G-quartet oligodeoxynucleotides Stat3 inhibitor.

Cancers that can be treated by this method preferably are those known or confirmed to contain CSCs, which include, but are not limited to: breast cancer, head and neck cancer, lung cancer, ovarian cancer, pancreatic cancer, multiple myeloma, colorectal carcinoma, prostate cancer, melanoma, kaposi sarcoma, ewing's sarcoma, liver cancer, gastric cancer, medulloblastoma, brain tumors, and leukemia.

The "second anti-cancer agent" in methods according to the third aspect of the invention can be the same "second anti-cancer agent" in methods according to the second aspect of the invention, and all the shared features are not repeated here.

In one embodiment, the second agent is a standard first-line treatment for at least one cancer. The second agent can be a cytotoxic agent. In one feature, the anti-cancer agent is a DNA-damaging agent, an anti-mitotic agent, and/or an anti-metabolite agent. For example, the DNA-damaging agent can be an alkylating agent, a topoisomerase inhibitor, or a DNA intercalator. In one embodiment, the second agent is one of carboplatin, doxorubicin, gemcitabine, docetaxel, or etoposide.

According to a fourth aspect of the invention, a method is provided for treating cancer in a subject, comprising the steps of: (a) administering to the subject a first amount of a first cancer stem cell inhibitor to inhibit Stat3 pathway activities; and (b) administering to the subject a second amount of a second cancer stem cell inhibitor to inhibit activities of a different pathway.

In an embodiment, the second cancer stem cell inhibitor is lapatinib. In some embodiments, the second amount of the second anti-cancer agent is not therapeutically effective against the cancer stem cell population by itself. Cancers that can be treated by this method preferably are those known or confirmed to contain CSCs and some examples are listed above. In various embodiments, the cancer is metastatic, refractory to a standard first-line cancer treatment, or relapsed.

According to a fifth aspect of the invention, a method is provided for treating cancer in a subject, comprising the steps of: (a) administering to the subject a therapeutically effective amount of a first anti-cancer agent selected from the group consisting of 2-(1-hydroxyethyl)naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, and a pharmaceutically acceptable salt or solvate thereof; and (b) administering a second anti-cancer agent that is not selected from the same group.

The second anti-cancer agent can be any of the agents described in other aspects of the invention, including any of the cytotoxic or chemotherapeutic agents, and any of the targeted agents.

In a sixth aspect, the present invention provides a pharmaceutical composition comprising a therapeutically effective amount of a first anti-cancer agent selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, and a pharmaceutically acceptable salt or solvate thereof; and a second anti-cancer therapy selected from the group consisting of a cytotoxic agent, a targeted agent, a radiotherapy agent, a biologic agent, a hormonal agent, a HDAC inhibitor, a retinoid agent, a checkpoint activator, a proteasome inhibitor, an adjuvant agent, or an adjunctive agent.

In an embodiment, the composition further includes a pharmaceutically-acceptable excipient, carrier, or diluent.

Other aspects including all compositions and kits related to methods described herein, and embodiments of the present invention are set forth or will be readily apparent from the following detailed description of the invention.

DETAILED DESCRIPTION

Figure 1:
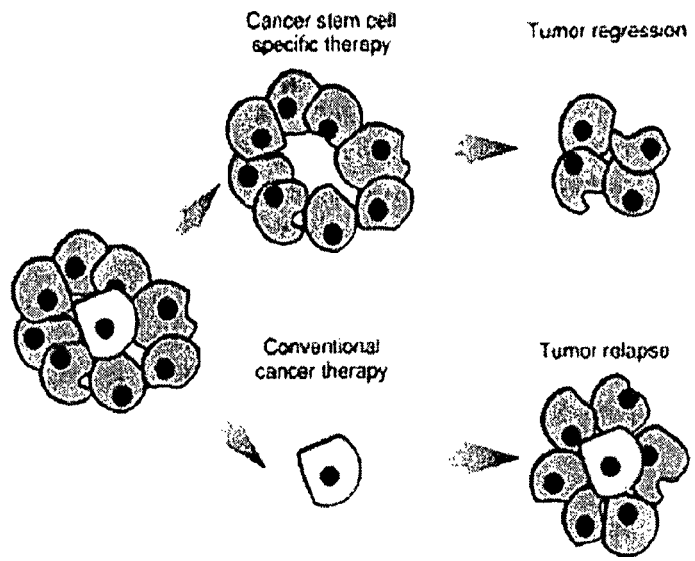
FIG. 1 illustrates the differences between cancer-stem-cell-specific and conventional cancer therapies.
Figure 2:
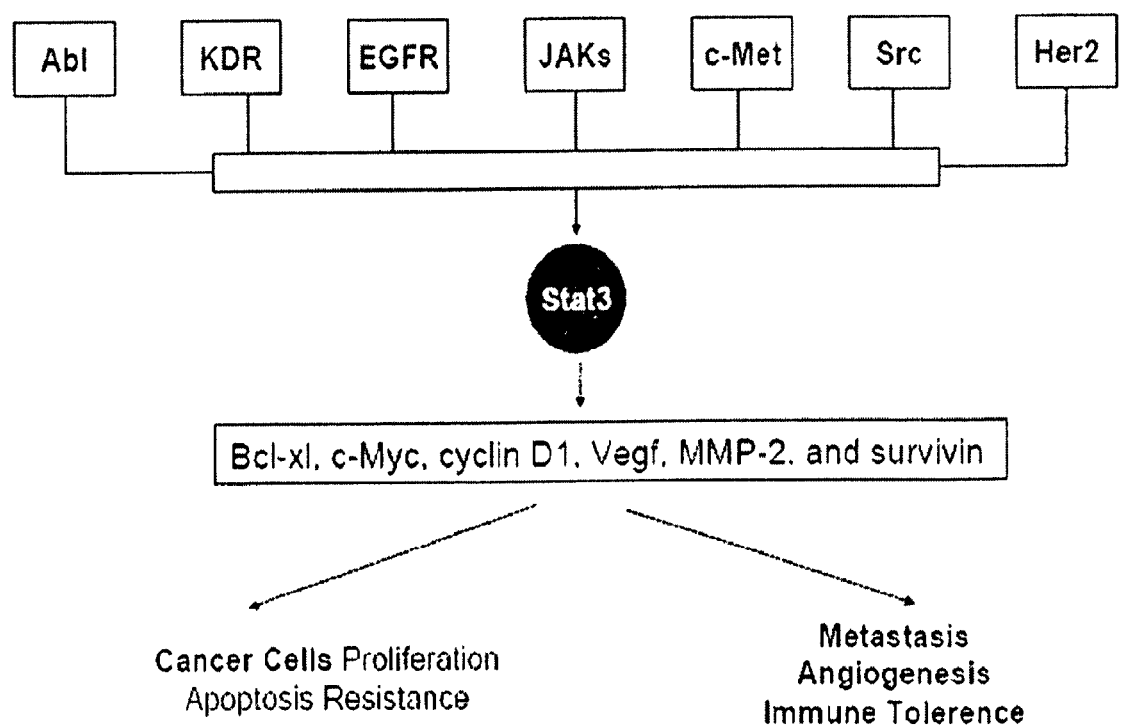
FIG. 2 shows the Stat3 pathway in cancer.

As used herein, the singular form "a", "an", and "the" include plural references unless the context clearly dictate otherwise. For example, the term "a cell" includes a plurality of cells including mixtures thereof.

The terms "isolated" or "purified" as used herein refer to a material that is substantially or essentially free from components that normally accompany it in its native state. Purity and homogeneity are typically determined using analytical chemistry techniques such as polyacrylamide gel electrophoresis or high performance liquid chromatography.

As used herein, the terms "cancer stem cell(s)" and "CSC(s)" are interchangeable. CSCs are mammalian, and in preferred embodiments, these CSCs are of human origin, but they are not intended to be limited thereto. Cancer stem cells are defined and functionally characterized as a population of cells originating from a solid tumor that: (1) have extensive proliferative capacity; 2) are capable of asymmetric cell division to generate one or more kinds of differentiated progeny with reduced proliferative or developmental potential; and (3) are capable of symmetric cell divisions for self-renewal or self-maintenance. Other common approaches to characterize CSCs involve morphology and examination of cell surface markers, transcriptional profile, and drug response. CSCs are also called in the research literature tumor/cancer initiating cells, cancer stem-like cells, stem-like cancer cells, highly tumorigenic cells, tumor stem cells, solid tumor stem cells, drug survival cells (DSC), drug resistant cells (DRCs) or super malignant cells.

As used herein, the term "self-renewal" refers to cancer stem cells' ability to give rise to new tumorigenic cancer stem cells to replenish or increase their number.

As used herein, the terms "cancer" and "cancerous" refer to or describe the physiological condition in mammals in which a population of cells are characterized by unregulated cell growth. "Cancer cells" and "tumor cells" as used herein refer to the total population of cells derived from a tumor including both non-tumorigenic cells, which comprise the bulk of the tumor cell population, and tumorigenic stem cells (cancer stem cells). Examples of cancer include, hut are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, various types of head and neck cancer, Esophageal cancer, and dermatological cancer.

"Tumor" as used herein refers to any mass of tissue that result from excessive cell growth or proliferation, either benign (noncancerous) or malignant (cancerous) including pre-cancerous lesions.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Terms such as "treating" or "treatment" or "to treat" or "alleviating" or "to alleviate" as used herein refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus those in need of treatment include those already with the disorder; those prone to have the disorder; and those in whom the disorder is to be prevented. A subject is successfully "treated" according to the methods of the present invention if the patient shows one or more of the following: a reduction in the number of or complete absence of cancer cells; a reduction in the tumor size; inhibition of, or an absence of cancer cell infiltration into peripheral organs including the spread of cancer into soft tissue and bone; inhibition of, or an absence of tumor metastasis; inhibition or an absence of tumor growth; relief of one or more symptoms associated with the specific cancer; reduced morbidity and mortality; and improvement in quality of life.

As used herein, the term "inhibiting", "to inhibit" and their grammatical equivalents, when used in the context of a bioactivity, refer to a down-regulation of the bioactivity, which may reduce or eliminate the targeted function, such as the production of a protein or the phosphorylation of a molecule. In particular embodiments, inhibition may refers to a reduction of about 20%, 30%, 40%, 50%, 60%, 70%, 80%, 90% or 95% of the targeted activity. When used in the context of a disorder or disease, the terms refer to success at preventing the onset of symptoms, alleviating symptoms, or eliminating the disease, condition or disorder.

"Normal cancer cells," as used herein either in singular or plural form, refers to cancer cells that are not cancer stem cells.

"Combination" or "combinatorial" therapy or treatment, as used herein means the administration of at least two different therapeutics to treat a disorder, condition or symptom, e.g., a cancer condition. Such combination therapy may involve the administration of one therapeutic before, during, and/or after the administration of the other therapeutic. The administrations of the therapeutics may be separated in time by up to several weeks, but more commonly within 48 hours, and most commonly within 24 hours.

The term "pharmaceutically-acceptable excipient, carrier, or diluent" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

The compounds of the present invention may form salts which are also within the scope of this invention. Reference to a compound of the present invention herein is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound I, II or III with an amount of acid or base, such as an equivalent amount, in a medium such as one in which the salt precipitates or in an aqueous medium followed by lyophilization.

Solvates of the compounds of the invention are also contemplated herein. Solvates of the compounds of the present invention include, for example, hydrates.

Targeting Stat3 Pathway

The present invention provides compounds that are effective inhibitors of Stat3 pathway activities (Example 2). As Stat3 pathway is a latent transcription factor activated to promote proliferation, survival and many other biological processes, it is implicated in a wide variety of human cancers as well as non-cancer disorders including a number of autoimmune and inflammatory diseases (Table 1). Accordingly, the present invention provides, in a first aspect, combination treatment of disorders associated with aberrant, e.g., over-expressed, Stat3 pathway activity. Specifically, the patient subject is administered a first amount of a first agent to inhibit at least some of the aberrant Stat3 pathway activity and also a second amount of a second agent which includes a signal transduction inhibitor. In various embodiments, some (e.g., 20%, 30%, 40%), most (more than about 50%), or substantially all (e.g., 60%, 70%, 80%, 90%, 95% or 100%), of the aberrant Stat3 pathway activity is inhibited. One or both of the first amount and the second amount can be a therapeutically effective amount of the respective agent before combination use, i.e., when used by itself against the disorder, or less than that amount because of outstanding synergistic effects from the combination. The first agent may target one or multiple steps in the Stat3 pathway. In one embodiment, the first agent is the Compound of the Invention.

TABLE 1

| Activation of STAT3 PATHWAY in human diseases | | | |
|---|---|---|---|
| | | DISEASES | REF. |
| ONCOLOGY DISEASES | Solid Tumors | Breast Cancer | [40] |
| | | Head and Neck Cancer (SCCHN) | [41] |
| | | Lung Cancer | [42] |
| | | Ovarian Cancer | [43] |
| | | Pancreatic Cancer | [44] |
| | | Colorectal carcinoma | [45] |
| | | Prostate Cancer | [46] |
| | | Renal Cell carcinoma | [47] |
| | | Melanoma | [48] |
| | | Hepatocellular carcinomas | [36] |
| | | Cervical Cancer | [49] |
| | | Endometrial Cancer | [49] |
| | | Sarcomas | [50, 51] |
| | | Brain Tumors | [52] |
| | | Gastric Cancers | [29] |

TABLE 1-continued

Activation of STAT3 PATHWAY in human diseases

| | | DISEASES | | REF. |
|---|---|---|---|---|
| | Hematologic Tumors | Multiple Myeloma | | [53] |
| | | Leukemia | HTLV-1-dependent Leukemia | [54] |
| | | | Chronic Myelogenous Leukemia | [47] |
| | | | Acute Myelogenous Leukemia | [55] |
| | | | Large Granular Lymphocyte Leukemia | [56] |
| | | Lymphomas | EBV-related/Burkitt's | [57] |
| | | | Mycosis Fungoides | [47] |
| | | | HSV Saimiri-dependent (T-cell) | [47] |
| | | | Cutaneous T-cell Lymphoma | [58] |
| | | | Hodgkin's Diseases | [47] |
| | | | Anaplastic Large-cell Lymphoma | [59] |
| IMMUNE DISEASES | Inflammatory Diseases | Inflammatory Bowel Diseases | | [60] |
| | | Inflammatory Arthritis | | [61-63] |
| | | Crohn's Diseases | | [64] |
| | | Chronic inflammatory conditions | | [65] |
| | Autoimmune | Reumatoid Arthritis | | [61, 62, 66-68] |
| | | Systemic lupus erythematosus | | [69] |
| | Asthma | | | [70] |
| | Allergy | | | [71] |
| | Infections | | | [72] |
| PROLIFERA- | Psoriasis | | | [73] |
| TIVE | Keloids | | | [74] |
| DISORDERS | Warts | | | [75] |
| | Myelodysplastic syndrome | | | [76] |
| | Polycythernia vera | | | [77] |
| CNS | Alzhemer's | | | [38, 78, 79] |
| DISEASES | Multiple sclerosis (MS) | | | [38, 78, 80] |

The second agent, i.e., a signal transduction inhibitor, can be used to target a different pathway, a related pathway or a different step in the same Stat3 pathway from the one inhibited by the first agent. Normally, when the two agents in the combination therapy target the same pathway, albeit at different steps, the expected amount of synergism is limited. However, data provided below in Example 5 show surprisingly high amounts of synergism between the Compound of the Invention and a second agent that presumably targets other steps in the same pathway, e.g., tyrosine kinases and GFR-targeting agents, suggesting unexpected mechanism of inhibition at work.

Specifically, Stat3 is activated by phosphorylation of a critical tyrosine residue mediated by growth factor receptor tyrosine kinases, Janus kinases, or the Src family kinases, etc; upon tyrosine phosphorylation, Stat3 forms homodimers, translocates to the nucleus, binds to specific DNA-response elements in the promoter regions of the target genes, and induces gene expression. Example 2 of the present invention shows that in the Stat3 pathway, the inhibitory effect by the Compound of the Invention is evident by the step of DNA-binding. Further, because such effect is found on constitutively activated Stat3, it is likely, that the Compound of the Invention inhibits dimerization and/or nuclear translocation of the Stat3 protein. Therefore, when combined with tyrosine kinases (TKI) and GFR-targeting agents that also target the same Stat3 pathway, the amount of synergism observed was surprisingly high. For example, 100% inhibition of cells from a pancreatic cancer cell line was achieved when Compound 401 was combined with TKI Sorafenib, whereas both Compound 401 and Sorafenib could only respectively achieve 66% inhibition of the same cell line when administered individually—pancreatic cancer is known to implicate over-expression of Stat3 [44]. In fact, all four TKIs tested in combination with Compound 401 showed marked synergism. In preferred embodiments of the invention, the combination treatment achieves over about 50%, or 70%, or 90% inhibition of the cancer cells.

Methods according to this first aspect of the invention can be applied to treatment of cancers or non-cancer disorders, preferably those known to be associated with aberrant Stat3 pathway activities. Examples of non-cancer disorders associated with aberrant Stat3 pathway activities include but are not limited to: autoimmune diseases, inflammatory diseases, inflammatory bowel diseases, arthritis, asthma, and systemic lupus erythematosus, autoimmune demyelination disorder, Alzheimer's disease, stroke, ischemia reperfusion injury and multiple sclerosis. Examples of cancers associated with aberrant Stat3 pathway activities include but are not limited to: breast cancer, head and neck cancer, lung cancer, ovarian cancer, pancreatic cancer, colorectal carcinoma, prostate cancer, renal cell carcinoma, melanoma, hepatocellular carcinomas, cervical cancer, sarcomas, brain tumors, gastric cancers, multiple myeloma, leukemia, and lymphomas.

The second agent according to this first aspect of the invention can be a targeted agent, e.g., a growth factor receptor-targeting agent (see erlotinib (tarceva) data in Example 5), a kinase-targeting agent (see lapatinib, erlotinib, sunitinib and sorafenib data in Example 5) or an angiogenesis inhibitor (see sunitinib and sorafenib data in Example 5).

In one embodiment, the second agent is a growth factor receptor-targeting agent, for example, an antibody targeting a growth factor receptor associated with a kinase, such as the Epidermal Growth Factor Receptor (EGFR) or the Vascular Endothelial Growth Factor Receptor (VEGFR). For example, the target agent can be gefitinib (Iressa), erlotinib (tarceva), PD153035, cetuximab (erbitux), avastin, panitumumab, trastuzumab, and anti-c-Met antibody.

In one embodiment, the second agent is a kinase-targeting agent, which can be a kinase inhibitor such as a tyrosine kinase inhibitor (TKI). For example, the TKI can be erlotinib (Tarceva), sutent (sunitinib), lapatinib, sorafenib (nexavar), vandetanib, axitinib, bosutinib, cedivanib, dasatinib (sprycel), gefitinib (irressa), imatinib (gleevac), lestaurtinib, and/or ARQ197.

In various embodiments, the kinase-targeting agent is one of the following: gefitinib (iressa), ZD6474 (AZD6474), EMD-72000 (matuzumab), panitumab (ABX-EGF), CI-1033 (PD183805), lapatinib (tykerb), AEE788 (pyrrolo-pyrimidine), EKB-569, EXEL 7647/EXEL 0999, erlotinib (tarceva), imatinib (gleevec), sorafinib (nexavar), sunitinib (sutent), dasatinib (sprycel), vandetinib (ZACTIMA), tem-sirolimus (torisel), PTK787 (vatalanib), pazopanib, AZD2171, everolimus, seliciclib, AMG 706, axitinib, PD0325901, PKC-412, CEP701, XL880, bosutinib, BIBF1120, BIBF1120, nilotinib, AZD6244, HKI-272, MS-275, BI2536, GX15-070, AZD0530, enzastaurin, MLN-518, and ARQ197.

In one embodiment, the second agent is an angiogenesis inhibitor which can be one of the following: CM101, IFN-α, IL-12, platelet factor-4, suramin, SU5416, thrombospondin, VEGFR antagonists, angiostatic steroids plus heparin, Cartilage-Derived Angiogenesis Inhibitory Factor, matrix metalloproteinase inhibitors, batimastat, marimastat, angiostatin, endostatin, 2-methoxyestradiol, tecogalan, thrombospondin, αVβ3 inhibitors, linomide, and ADH-1.

In a related second aspect, the present invention provides a method of treating a subject of a cancer that is associated with aberrant Stat3 pathway activity, the method comprising the steps of (a) administering to the subject a first amount of a first agent to inhibit at least some of the aberrant Stat3 pathway activity; and (b) administering to the subject a second amount of a second anti-cancer agent. Cancers that can be treated with this method include those known to be associated with, e.g., caused at least partly by, aberrant Stat3 pathway activities, a list of which is provided above with regard to the first aspect of the invention.

While features regarding the first agent can be similar to those described with regard to the first aspect of the invention, the second anti-cancer agent can be a cytotoxic agent, or, a chemotherapeutic agent. In one embodiment, the second agent is a standard first-line treatment for at least one cancer. The amount of the first agent and second agent used in the method can be a therapeutically effective amount of the respective agent before combination use or less.

In one feature, the anti-cancer agent is a DNA-damaging agent, an antimitotic agent, and/or an antimetabolite agent. The DNA-damaging agent can be an alkylating agent, a topoisomerase inhibitor, and/or a DNA intercalator. As shown in Example 5, Compound 401 of the present invention was added to Paca2 pancreatic cancer cells along with each of the following: carboplatin (a DNA-alkylating agent), etoposide (inhibitor of topoisomerase II), doxorubicin (a DNA intercalator), docetaxel (an anti-mitotic agent), and Gemzar/gemcitabine (an anti-metabolite agent). Significant amount of synergism was found in each combination. For example, 96% inhibition of the pancreatic cancer cells was achieved when Compound 401 was combined with Gemzar/gemcitabine whereas Compound 401 and Gemzar could only respectively achieve 66% and 36% inhibition of the same cell line when administered individually.

The alkylating agent can be one of the following: chlorambucil, cyclophosphamide, ifosfamide, mechlorethamine, melphalan, uracil mustard, thiotepa, busulfan, carmustine, lomustine, streptozocin, carboplatin, cisplatin, satraplatin, oxaliplatin, altretamine, ET-743, XL119 (becatecarin), dacarbazine, chlormethine, bendamustine, trofosfamide, uramustine, fotemustine, nimustine, prednimustine, ranimustine, semustine, nedaplatin, triplatin tetranitrate, mannosulfan, treosulfan, temozolomide, carboquone, triaziquone, triethylenemelamine, and procarbazin.

The topoisomerase inhibitor can be one of the following: doxorubicin (doxil), daunorubicin, epirubicin, idarubicin, anthracenedione (novantrone), mitoxantrone, mitomycin C, bleomycin, dactinomycin, plicatomycin, irinotecan (camptosar), camptothecin, rubitecan, belotecan, etoposide, teniposide, and topotecan (hycamptin).

The DNA intercalator can be proflavine, doxorubicin (adriamycin), daunorubicin, dactinomycin, and thalidomide.

The antimitotic agent can be one of the following: paclitaxel (abraxane)/taxol, docetaxel (taxotere), BMS-275183, xyotax, tocosal, vinorlebine, vincristine, vinblastine, vindesine, vinzolidine, etoposide (VP-16), teniposide (VM-26), ixabepilone, larotaxel, ortataxel, tesetaxel, and ispinesib.

The antimetabolite agent can be one of the following: fluorouracil (5-FU), floxuridine (5-FUdR), methotrexate, xeloda, arranon, leucovorin, hydroxyurea, thioguanine (6-TG), mercaptopurine (6-MP), cytarabine, pentostatin, fludarabine phosphate, cladribine (2-CDA), asparaginase, gemcitabine, pemetrexed, bortezomib, aminopterin, raltitrexed, clofarabine, enocitabine, sapacitabine, and azacitidine.

In one embodiment, the second anti-cancer agent is one of the following: carboplatin, doxorubicin, gemcitabine, docetaxel, and etoposide. As this method inhibits Stat3 pathway, proven herein to be critical for both the self-renewal and survival of CSCs (see data in Example 1), and CSCs have been found to be fundamentally responsible for drug resistance, tumor relapse and metastasis, in preferred embodiments, this method is used to treat or prevent a refractory cancer, relapsed cancer and/or metastatic cancer.

Further discussions of anticancer chemotherapy and biologic therapy, and examples of suitable therapeutic protocols, may be found in such books as *Cancer Chemotherapy and Biotherapy: Principles and Practice*, 3rd ed. (2001), Chabner and Longo, eds., and *Handbook of Cancer Chemotherapy*, 6th ed. (2003), Skeet, ed., both from Lippincott Williams & Wilkins, Philadelphia, Pa., U.S.A.; and regimens for anticancer therapies, especially chemotherapies, may be found on Web sites such as those maintained by the National Cancer Institute (www.cancer.gov), the American Society for Clinical Oncology (www.asco.org), and the National Comprehensive Cancer Network (www.nccn.org).

Targeting Cancer Stem Cells

The present invention also provides both in vitro and in vivo data that the Compound of the Invention inhibits CSCs' self-renewal and is apoptotic to CSCs (Example 3). Moreover, the present invention empirically confirms the Compound of the Invention's efficacy against metastatic cancer (Example 4).

The purpose of cancer therapy (anticancer therapy) is to prevent cancer cells from multiplying, invading, metastasizing, and ultimately killing their host organism, e.g. a human or other mammals. Because cell multiplication is a characteristic of many normal cells as well as cancer cells, most of the existing anticancer therapies also have toxic effects on normal cells, particularly those with a rapid rate of turnover, such as bone marrow and mucous membrane cells. Therefore, an effective cancer therapy needs to have a marked growth inhibitory or controlling effect on the cancer cells while exerting a minimal toxic effect on the host's normal cells.

Since the first effective anticancer compounds were brought into clinical trials in the 1940's, cancer relapse and drug resistance have remained some of the biggest problems in cancer treatment. Often, regressions of symptoms can be obtained, but responses are frequently partial and only of short duration, and relapsed cancers tend to be resistant to the original drug. This can now be explained by the existence of cancer stem cells (CSCs). As described above, this tiny population of cells within the entire cancer mass can evade drugs and radiotherapies that are effective on the rest of the cancer cells because CSCs probably share the same kind of biological mechanisms with normal somatic stem cells, which are naturally resistant to most, if not all, of the chemotherapeutic agents. Being the true root of tumorigenic activities in cancer masses, CSCs can re-espouse cancer regrowth or cause metastasis if left untreated. Since the initial treatment leaves only drug-resistant cancer stem cells, chances for the entire regrown or metastatic tumor to become resistant to the initially "effective" therapy have dramatically increased.

Presently, anticancer therapies are used in combination for several reasons. First, treatment with two or more non-cross-resistant therapies may prevent the formation of resistant clones in the tumor. Resistance to one anticancer drug, e.g. a platinum anticancer compound such as cisplatin, is often associated with cross-resistance to other drugs of the same class, e.g. other platinum compounds. Further, there is also multiple drug resistance, also called pleiotropic drug resistance, where treatment with one drug confers resistance not only to that drug and others of its class but also to unrelated agents. Second, the combination of two or more therapies that are active against cells in different phases of growth may kill cells that are dividing slowly as well as those that are dividing actively and/or recruit cells into a more actively dividing state, making them more sensitive to multiple anticancer therapies. And third, the combination may create a biochemical enhancement effect by affecting different pathways or different steps in a single biochemical pathway.

These rationales for combinational anti-cancer treatment have not taken into account recent advances in confirming and characterizing cancer stem cells. The failure to incorporate a CSC-specific therapy in the combination therapy could explain why current combination therapies cannot cure common cancers such as metastatic colon cancer and prostate cancer. With data provided herein that confirms the efficacy of the Compound of the Invention against CSCs (Example 3), the present invention is able to devise a cancer treatment method that combines a CSC-targeting agent and another agent targeting normal cancer cells. Further, while not wishing to be bound by a particular theory, the present invention provides a drug regimen that preempts the scenario, which is now supported by some preliminary data, where some normal cancer cells, left untreated or insufficiently treated, revert back or give rise to CSCs as the original CSCs get depleted by a single-drug therapy that targets CSCs only.

Since cancer stem cells are generally resistant to radiotherapy and conventional chemotherapies, a drug that targets cancer stem cells should have synergistic effect when used in combination with other anti-cancer therapies. Therefore, the present invention provides a method of treating cancer in a subject, comprising the steps of: (a) administering to the subject a first amount of a first anti-cancer agent to inhibit a cancer stem cell population; and (b) administering to the subject a second amount of a second anti-cancer agent to inhibit a plurality of normal cancer cells.

In various embodiments, some (e.g., 20%, 30%, 40%), most (more than about 50%), or substantially all (e.g., 60%, 70%, 80%, 90%, 95% or 100%), of the CSCs are inhibited. One or both of the first amount and the second amount can be a therapeutically effective amount of the respective agent before combination use, i.e., when used by itself against the cancer, or less than that amount because of outstanding synergistic effects from the combination. In one embodiment, the first agent is the Compound of the Invention, namely, 2-(1-hydroxyethyl)-naphtho[2,3-b]furan-4,9-dione, 2-Acetyl-7-Chloro-naphtho[2,3-b]furan-4,9-dione, 2-Acetyl-7-Fluoro-naphtho[2,3-b]furan-4,9-dione, 2-acetyl-naphtho[2,3-b]furan-4,9-dione, 2-ethyl-naphtho[2,3-b]furan-4,9-dione, and a pharmaceutically acceptable salt or solvate thereof.

The "second anti-cancer agent" here can be the same "second anti-cancer agent" in methods described above, and all the shared features are not repeated here. In one feature, the second anti-cancer agent is a DNA-damaging agent, an antimitotic agent, and/or an antimetabolite agent. For example, the DNA-damaging agent can be an alkylating agent, a topoisomerase inhibitor, or a DNA intercalator. Lists of suitable alkylating agents, topoisomerase inhibitors, DNA intercalators, antimitotic agents, and antimetabolite agents are listed above and are not repeated here. Significant synergism was observed in cancer-inhibition experiments where the Compound of the Invention is used in combination with each of the above classes of chemotherapeutic agents (see Example 5). In one embodiment, the second agent is one of carboplatin, doxorubicin, gemcitabine, docetaxel, and etoposide.

In another feature, the second anti-cancer agent is targeted agent, e.g., a growth factor receptor-targeting agent (see erlotinib (tarceva) data in Example 5), a kinase-targeting agent (see lapatinib, erlotinib, sunitinib and sorafenib data in Example 5) or an angiogenesis inhibitor (see sunitinib and sorafenib data in Example 5). Significant synergism was observed in cancer-inhibition experiments where the Compound of the Invention is used in combination with each of the above classes of targeted agents. Lists of suitable growth factor receptor-targeting agents, kinase-targeting agents (especially TKI), and angiogenesis inhibitors are listed above and not repeated here.

As this method employs a therapeutic agent specifically targeting CSC cells in the tumor, which are fundamentally responsible for drug resistance, tumor relapse and metastasis, in preferred embodiments, this method is used to treat or prevent a refractory cancer, relapsed cancer and/or metastatic cancer.

In targeting CSCs with a combination treatment, one strategy should aim at targeting more than one pathway that are implicated in CSC's critical biological functions such as self-renewal and survival. To that end, the present invention provides a method of treating cancer in a subject that includes the steps of: (a) administering to the subject a first amount of a first cancer stem cell inhibitor to inhibit Stat3 pathway activities; and (b) administering to the subject a second amount of a second cancer stem cell inhibitor to inhibit activities of a different pathway. In an embodiment, the amount of the first and/or second anti-cancer agent in this method is not therapeutically effective against the cancer stem cell population by itself—but due to significant synergism achieved through the combination, lower amount is able to be used in this method in order to elicit response from the patient.

In one embodiment, the second anti-cancer stem cell agent is lapatinib (INN) or lapatinib ditosylate (USAN), which was approved by the FDA in 2007 for use in patients with advanced metastatic breast cancer. Lapatinib is an ATP-competitive epidermal growth factor receptor (EGFR) and HER2/neu (ErbB-2) dual tyrosine kinase inhibitor. It inhibits receptor autophosphorylation and activation by binding to the ATP-binding pocket of the EGFR/HER2 protein kinase domain. Data presented in Example 5 below shows that marked synergism was achieved against Paca2 pancreatic cancer cells: pre-combination rate of inhibition for Compound 401 and lapatinib were respectively 32% and 27% while the rate of inhibition after combination shot up to 74%, higher than the sum of the two rates. As this method pays additional attention to CSCs, which are fundamentally responsible for drug resistance, tumor relapse and metastasis, in preferred embodiments, this method is used to treat or prevent a refractory cancer, relapsed cancer and/or metastatic cancer.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the mammal being treated and the particular mode of administration. The amount of active ingredient, which can be combined with a carrier material to produce a single dosage form, will generally be that amount of the compound which produces a therapeutic effect. Generally, out of 100%, this amount will range, for example, from about 1% to about 99% of active ingredient, from about 5% to about 70%, from about 10% to about 30%.

Materials and Methods

Biological Assays

Compounds of the present invention can be tested according to the protocol described above. Table 2 shows the list of compounds described in the protocol.

TABLE 2

| Compound Name | Compound Code |
| --- | --- |
| 2-(1-hydroxyethyl)-naphtho[2,3-b]furan-4,9-dione | 301 |
| 2-Acetyl-7-Chloro-naphtho[2,3-b]furan-4,9-dione | 416 |
| 2-Acetyl-7-Fluoro-naphtho[2,3-b]furan-4,9-dione | 418 |
| 2-acetylnaphtho[2,3-b]furan-4,9-dione | 401 |
| 2-ethyl-naphtho[2,3-b]furan-4,9-dione | 101 |

Cell Culture:

HeLa, DU145, H1299, DLD1, SW480, A549, MCF7, LN18, HCT116, HepG2, Paca2, Panel, LNcap, FaDu, HT29, and PC3 cells (ATCC, Manassas, Va.) were maintained in Dulbecco's Modified Eagle Medium (DMEM) (Invitrogen, Carlsbad, Calif.) supplemented with 10% fetal bovine serum (FBS) (Gemini Bio-Products, West Sacramento, Calif.) and 5% penicillin/streptomycin/amphotercin B (Invitrogen).

Hoechst Side Population:

To identify and isolate side population (SP) and non-SP fractions, SW480 cells were removed from the culture dish with trypsin and EDTA, pelleted by centrifugation, washed with phosphate-buffered saline (PBS), and resuspended at 37° C. in Dulbecco's modified Eagle's medium (DMEM) containing 2% FBS and 1 mM HEPES. The cells were then labeled with Hoechst 33342 (Invitrogen) at a concentration of 5 µg/mL The labeled cells were incubated for 120 minutes at 37° C., either alone or with 50 µM verapamil (Sigma-Aldrich, St. Louis). After staining, the cells were suspended in Hanks' balanced saline solution (HBSS; Invitrogen) containing 2% FBS and 1 mM HEPES, passed a through 40 µm mesh filter, and maintained at 4° C. until flow cytometry analysis. The Hoechst dye was excited at 350 nm, and its fluorescence was measured at two wavelengths using a 450 DF10 (450/20 nm band-pass filter) and a 675LP (675 nm long-pass edge filter) optical filter. The gating on forward and side scatter was not stringent, and only debris was excluded [15].

CSC Isolation with Surface Markers:

Sorting tumor cells based primarily upon the differential expression of the surface marker(s), such as CD44 or CD133, have accounted for the majority of the highly tumorigenic CSCs described to date. CD133 isolation is based upon the method of Ricci-Vitiani et al. [21], with slight modification. $CD133^+$ cells were isolated by either fluorescence activated cell sorting (FACS) or magnetic nanoparticle-based separation. Briefly, $10^7$ cells/mL were labeled with CD133/1 (AC133)-PE for FACS-based cell sorting; or with CD133/1 (AC133)-biotin (Miltenyi Biotec, Auburn, Calif.) for magnetic field-based separation using the EasySep® biotin selection kit (Miltenyi Biotec) according to the manufacturer's recommendations. Non-specific labeling was blocked with the supplied FcR blocking reagent and antibody incubations (1:11) were carried out on ice for 15 minutes in PBS with 2% FBS and 1 mM EDTA. Five washes were done for EasySep® isolation, whereas cells were pelleted at 400×g for 5 minutes and resuspended at $2 \times 10^7$/mL, before sorting by FACS.

$CD44^{high}$ cells were isolated by FACS according to the methods described in Ponti et al, with slight modification [81]. Briefly, after trypsinization and recovery of cells for 30 minutes at 37° C. in growth media, cells were pelleted at 400×g and were resuspended in PBS with 2% FBS and 1 mM EDTA at $1 \times 10^6$ cells/mL. Cells were then incubated on ice with a 1:100 dilution of CD44-FITC (BD Biosicences, San Diego, Calif.) for 15 minutes. Alternatively, CD24-PE (BD Biosciences, San Diego, Calif.) (1:100) was utilized for negative selection. After washing three times, cells were resuspended at $2 \times 10^6$/mL and passed through a 40 µM mesh before sorting Sphere Assay:

A reliable method of measuring the self-renewal capacity of cell population if the ability to be cultured as spheres in the absence of serum or attachment. $CD44^{high}$ FaDu or Hoechst side population cancer stem cells were cultured in ultra low attachment plates in cancer stem cell media (DMEM/F12, B27 Neurobasal supplement, 20 ng/ml EGF, 10 ng/ml FGF, 4 µg/ml insulin, and 0.4% BSA) to allow spheres formation. Typically, sphere formation was evaluated by microscopy after 10-14 days in culture and spheres with >50 cells were scored.

Luciferase Reporter Assay:

HeLa Cells were co-transfected with Stat3-luciferase (Stat3-Luc) reporter vector (Panomics, Fremont, Calif.) and Renilla luciferase (Promega, Madison, Wis.) using Lipofectamine 2000 as described by the manufacturer (Invitrogen). Following transfection, cells were maintained in medium containing 0.5% FBS for 24 hours. Cells were then treated with the indicated compound for 30 minutes prior to the addition of 25 ng/ml oncostatin M (OSM) (R&D Systems, Minneapolis, Minn.) to the medium. 6 hours following OSM addition, cells were harvested and levels of firefly and renilla luciferase were measured using the Dual-Glo Luciferase Assay System as described by the manufacturer (Promega).

Analysis of Apoptosis:

Cells treated with or without compound were harvested at 5 hours post treatment for Annexin-V staining. Collected cells were washed with PBS and resuspended in Annexin-V-FITC containing buffer and stained according to manufactures directions (Roche). Armexin-V positive cells were determined by Flow cytometry.

STAT3 DNA Binding Assay:

Electrophoretic mobility shift assay (EMSA) was performed as described by the manufacturer (Li-Cor Biosciences, Lincoln, Nebr.). Briefly, nuclear extracts were made from HeLa cells using the NucBuster Protein Extraction Kit as described by the manufacturer (EMD Biosciences, San Diego, Calif.). 5 µg of nuclear extract was pre-incubated with the indicated dose of indicated compound for 30 minutes prior to a 15-minute incubation with the IR700-labeled consensus Stat3 oligonucleotide. Samples were then electrophoresed on a polyacrylamide gel and directly scanned using the Odyssey infrared imaging system (Li-Cor Biosciences). For the enzyme-linked immunosorbent assay (ELISA), 5 µg of nuclear extract was preincubated with indicated concentration of indicated compound for 30 minutes prior to the addition of biotinylated oligo (5'-Biotin-GATCCTTCTGGGAATTCCTAGATC-3' SEQ ID NO. 1). Stat3-DNA complexes were then captured on streptavidin coated 96 well plates (Pierce, Rockford, Ill.). Bound complexes were then incubated with Stat3 polyclonal antibody (Santa Cruz Biotechnology, Santa Cruz, Calif.) followed by anti-rabbit HRP conjugated secondary antibody (GE Healthcare, Pittsburgh, Pa.). Bound antibody was then visualized by addition of TMB substrate (Pierce) and absorbance measured at 450 nm.

Cell Viability Determination:

For 3-(4,5 dimethylthiazol-2-yl)-2,5-diphenyltetrazolium (MTT) (Sigma-Aldrich, St. Louis, Mo.) analysis, cells were plated in 96 well plates at 10,000 cells per well. 24 hours after plating, compound was added to cells at indicated doses. 22 hours following compound addition, MTT was added to each well (0.5 mg/ml, final concentration) and plates were incubated for an additional 2 hours at 37° C. Medium was then aspirated and the formazan product was solubilized in 100 µl of isopropyl alcohol. The absorbance of each well was measured at 570 nm using a microplate reader.

Immunofluorescence:

Cells treated with indicated compound for an indicated time were either fixed in 4% formaldehyde or cold methanol for the detection of Annexin V, cleaved caspase 3, or stat3, respectively. Coverslips were air dried and rehydrated in PBS at room temperature for 10 min. Samples were then incubated in blocking buffer (PBS, 5% FBS) for 10 min at room temperature in a humid chamber. Cells were incubated overnight at 4° C. with primary antibodies. After washing, the cells were incubated for 1 hour at room temperature with a 1:500 dilution of FITC conjugated anti-rabbit antibody. Images were captured with a Nikon TE200 microscope equipped with epifluorescence and a SPOT mosaic CCD camerapolyclonal Anti-cleaved caspase 3 antibody (1:100) was obtained from Cell Signaling Technology, Danvers, Mass. Annexin-V-FITC was obtained from Roche, Penzberg, Germany. Polyclonal anti-Stat3 antibody was obtained from Santa Cruz.

Gene Knockdown by TPIV® Technology:

The TPIV® (Therapeutic Pathway Identification and Validation) technology (Boston Biomedical Inc., Norwood, Mass., USA) provides plasmids that can be used to first transfect bacteria that are in turn taken up by a mammalian subject. After bacterial lysis, dsRNA encoded by the TPIV® plasmids and processed by the bacteria get released into the mammalian cell cytoplasm and effect targeted gene knockdown. The TPIV® technology is described in co-owned PCT patent application no. PCT/US08/68866 filed on Jun. 30, 2008, the entire content of which is incorporated herein by reference. Specifically, a TPIV® plasmid that encodes effective siRNA sequences against Stat3 was constructed by PCR-cloning of a Stat3 plasmid purchased from Origene Technologies (Rockville, Md., USA) using the following primers:

TPIV-Stat3 (300 bp Insert)
Primers:

```
Stat3 TPIV For
5'-GGATCTAGAATCAGCTACAGCAGC    (SEQ ID NO. 2)

Stat3 TPIV Rev
5'-TCCTCTAGAGGGCAATCTCCATTG    (SEQ ID NO. 3)
```

The control plasmid is constructed using a pGL2 plasmid purchased from Promega (Madison, Wis., USA).

TPIV-GL2 (300 bp Insert)
Primers:

```
GL2 TPIV For
5'-CCCTCTAGATGGTTCCTGGAAC     (SEQ ID NO. 4)

GL2 TPIV Rev
5'-GCTCTAGAAACCCCTTTTTGG      (SEQ ID NO. 5)
```

Chemically competent *E. coli* BL21 (DE3) pLYSe bacteria (50~100 µl) were transformed with control or 100 ng of Stat3-targeting TPIV® plasmid according to the manufacturer instructions (Stratagene). A single colony was then inoculated into BHI medium containing 100 µg/ml ampicillin, and grown overnight at 37° C. The next day, 5 ml of each overnight culture was diluted 1:40 into fresh BHI medium containing 100 µg/ml ampicillin and grown for a further 2-4 hours (until the $OD_{600}$=0.5). Each culture was then treated with IPTG (1 mM final concentration) for 2-4 hours to induce transcription of the long double strand RNAs which would be processed into a cocktail siRNAs by the bacteria. After IPTG induction, the total number of bacteria in each culture was calculated by measuring the $OD_{600}$ value ($8\times10^8$ bacteria/ml culture has an $OD_{600}$=1). The number of bacteria for cell treatment was then calculated according to cell confluency and the needed multiplicity of infection (MOI; try ranges of 20:1 to 2000:1, bacteria to cells) in an appropriate reaction volume. As a rule of thumb, the reaction volume should be chosen to result in $3\times10^8$/ml for a 1000:1 MOI. The required volume of bacteria culture was then centrifuged at 2500 g for 10 mins at 4° C. and the pellet was washed once with serum-free culture medium that was used for the cells being bactofectioned plus 100 µg/ml ampicillin and 1 mM of IPTG, and resuspended in the same medium at the required density for bacterial infection (bactofection).

At the same time, cancer cells or cancer stem cells were isolated. 30 minutes before bactofection, the cell culture medium was replaced with 2 ml of fresh serum-free medium containing 100 µg/ml of ampicillin and 1 mM IPTG. Bacteria prepared above were then added to the cells at the desired MOI for 2 hours at 37° C.

After the infection period, the cells were washed 3 times using serum-free cell culture medium. The cells were then incubated with 2 ml of fresh complete cell culture medium containing 100 µg/ml of ampicillin and 150 µg/ml of gentamycin for 2 hours to kill any remaining extracellular bacteria. After treatment with ampicillin and gentamycin, the cells were incubated with 3 ml of fresh complete RPMI 1640 medium containing 10 µg/ml of ofloxacin to kill any intracellular bacteria. The cells were then harvested or analysis at various time points in order to assess the extent of target gene silencing and the resulting phenotypes.

In Life Evaluations:

Daily examinations into the health status of each animal were also conducted. Body weights were checked every three days. Food and water was supplied daily according to the animal husbandry procedures of the facility. Treatment producing >20% lethality and or >20% net body weight loss were considered toxic. Results are expressed as mean tumor volume (mm$^3$)±SE. P Values<0.05 are considered to be statistically relevant.

Animal Husbandry:

Male or female athymic nude mice 4-5 weeks (Charles River Laboratories, Wilmington, Mass.), were acclimated to the animal housing facility for at least 1 week before study initiation. All of the experimental procedures utilized were consistent with the guidelines outlined by the American Physiology Society and the Guide for the Care and Use of Laboratory Animals and were also approved by the Institutional Animal Care and Use Committee of Boston Biomedical Inc. The animals were housed in groups of four in wood chip bedded cages in a room having controlled temperature (68° F.-72° F.), light (12-h light-dark cycle), and humidity (45-55%). The animals were allowed free access to water and food during the experiment.

Intrasplenic-Nude Mouse Model System (ISMS Model):

The female nude mice were anesthetized and under aseptic conditions, an incision was made in the left flank to expose the spleen. One million human colon cancer HT29 cells in 0.1 ml PBS were injected under the spleen capsule using a 27-gauge needle. The spleen was replaced in the peritoneal cavity and the incision was closed. Treatment started the next day after the implantation till the examination day. The regimen of the treatments is 5 qd/wk via i.p. The mice were sacrificed when moribund or 30 days after the injection. The spleen and liver were removed and examined, and the number of tumor lesions was recorded.

Example 1

Identification of Stat3 as an Anti-Cancer Stem Cell Target

Figure 3A:
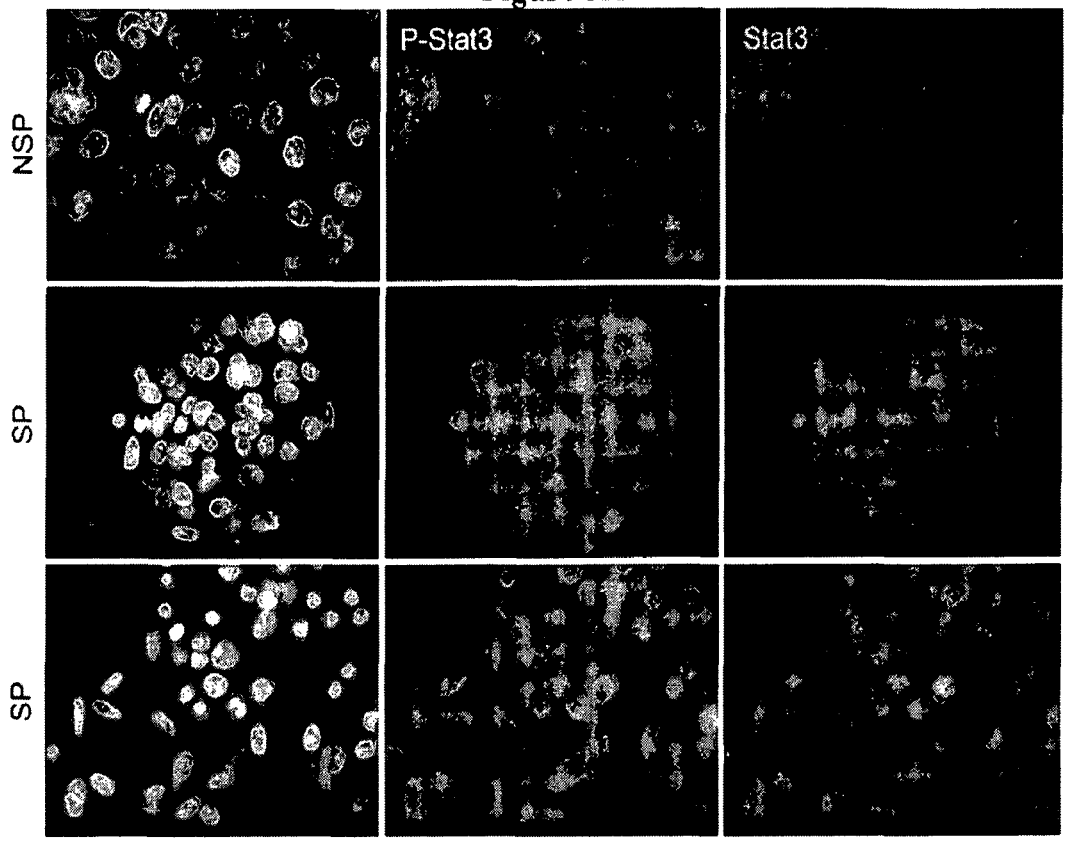
FIG. 3A shows that Stat3 is constitutively active in Hoechst Side Population cells.

Stat3 knockdown in CSCs induces apoptosis. To determine whether cancer stem cells expressed Stat3 and whether Stat3 was constitutively active, we performed immunofluorence microscopy, which allows not only the analysis of rare cell populations, but also provides additional information on protein localization and the ability to correlate staining with phenotype (i.e. apoptosis). Following immunofluorescent detection of p-Stat3 and Stat3 in NSP and SP cells isolated by FACS from SW480 colon cancer cells, we determined that Stat3 was indeed present in SP cells and that it was modestly enriched in the nucleus (FIG. 3A). In addition, we also observed increased p-Stat3 staining in SP cells over NSP cells, suggesting that SP cells may rely more heavily on Stat3 for survival.

Figure 3B:
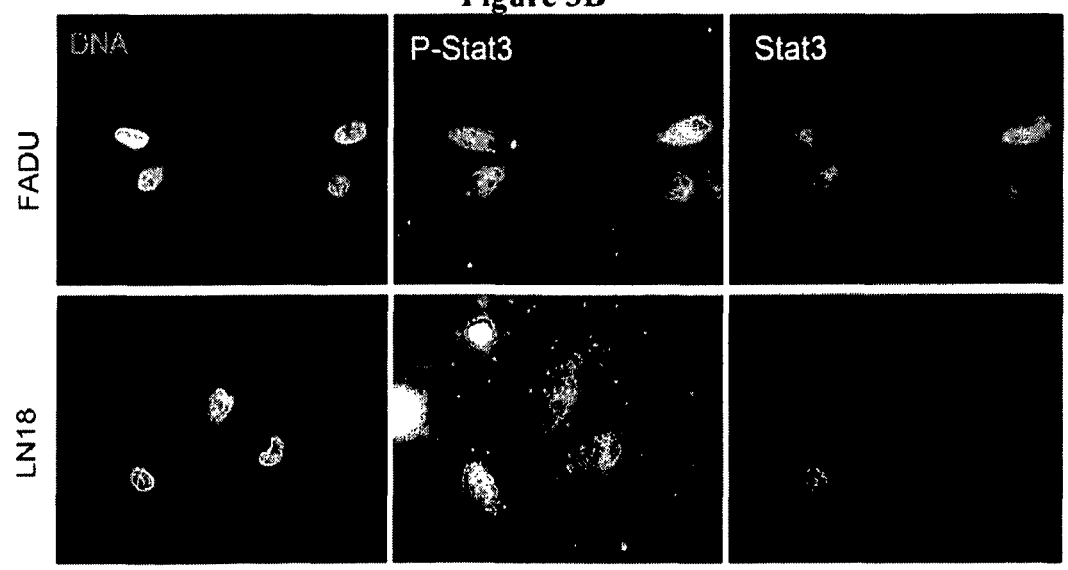
FIG. 3B shows that Stat3 is constitutively active in CD133+ cells.

The status of Stat3 was also evaluated in CD133$^+$ cells isolated from FaDu human head and neck cancer cells and LN18 human glioblastoma cells. As shown in FIG. 3B, Stat3 are also constitutively active in these cells. Taken together, these data suggest Stat3 as a target that is particularly important for cancer stem cells.

Figure 4A:
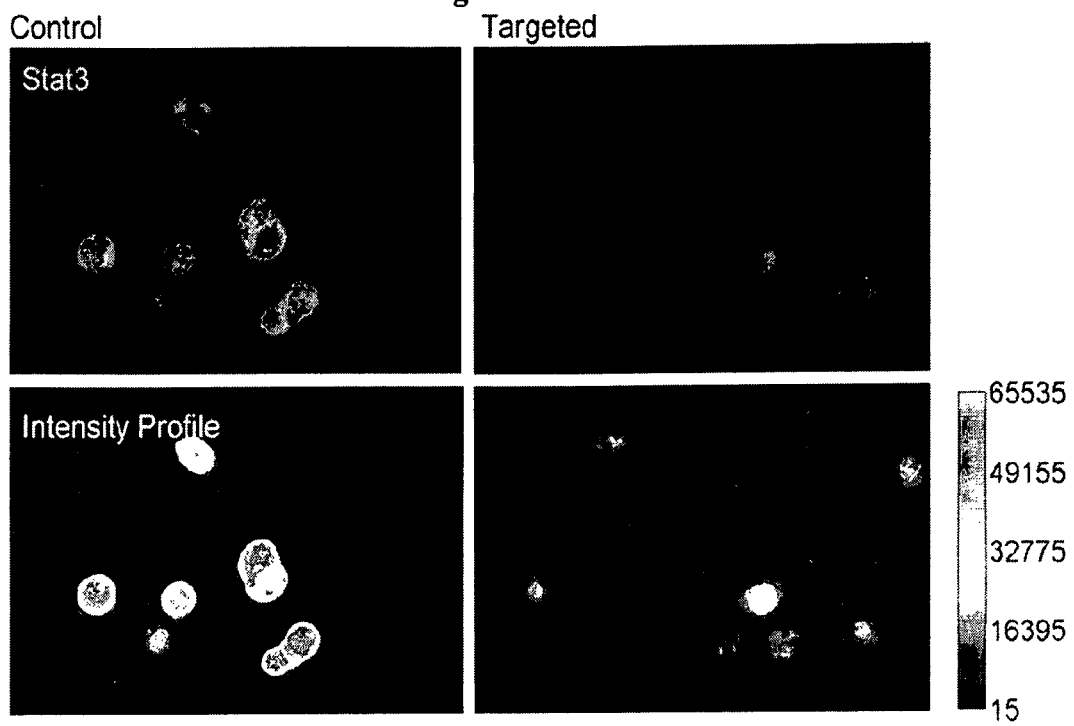
FIGS. 4A and 4B show that Stat3 knockdown in cancer stem cells induces apoptosis.
Figure 4B:
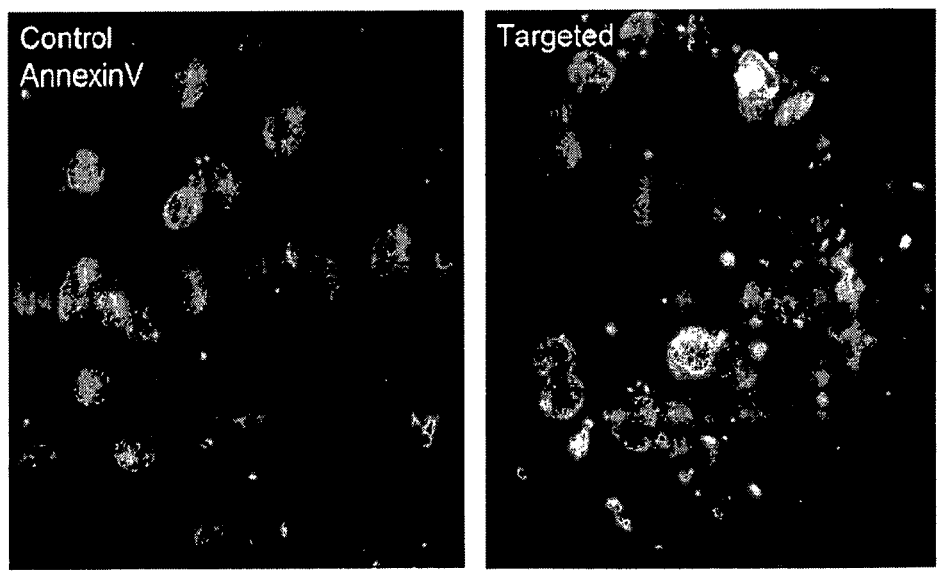

We next tested the effect of Stat3 knockdown in CSCs using TPIV®. Immunofluorescence analysis revealed that significant depletion of Stat3 could be achieved within 24 hours of infection (FIG. 4A) on freshly isolated CSCs (SP) and found that the majority of cells treated with Stat3-targeting TPIV® plasmids underwent apoptosis within 24 hours of infection, whereas control TPIV® plasmids did not induce apoptosis to levels above control, uninfected cells (FIG. 4B). These data demonstrate that cancer stem cells depend upon Stat3 for survival.

Knock Down Stat3 in CSCs Inhibits CSC Spherogenesis.

Figure 5:
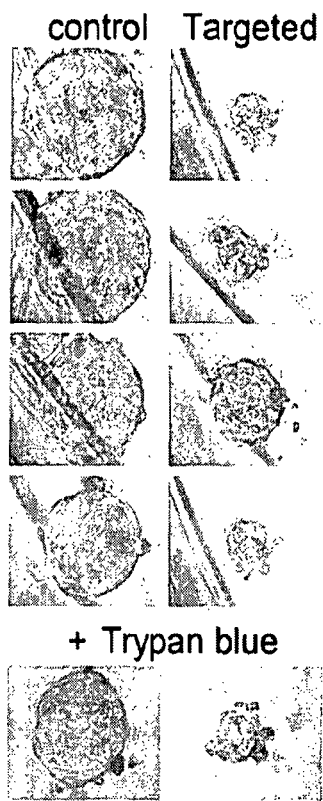
FIG. 5 shows that Stat3 knockdown in cancer stem cells inhibits cancer stem cell spherogenesis.
Figure 5:
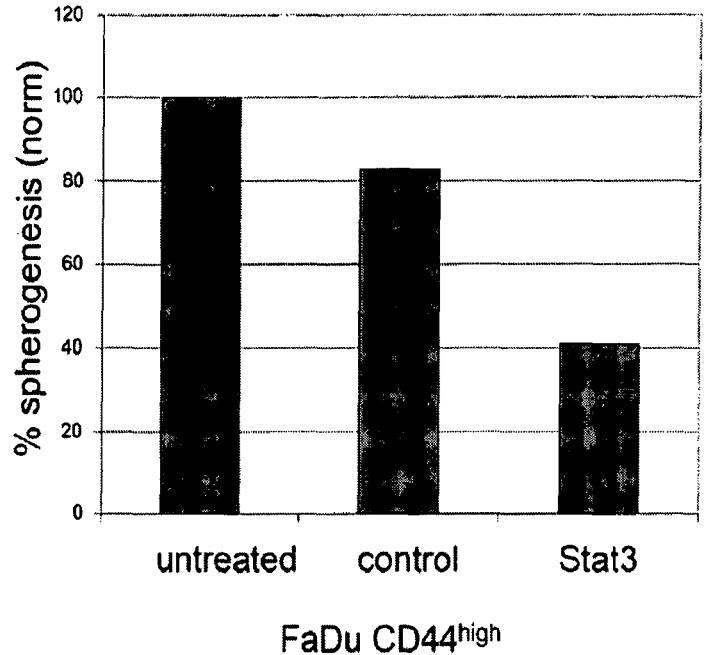

CD44$^{high}$/CD24$^{low}$ FaDu or Hoeschst side population cancer stem cells were isolated by FACS, and cultured in ultra low attachment plates in cancer stem cell media (DMEM/F12, B27 Neurobasal supplement, 20 ng/mL EGF, 10 ng/mL FGF, 4 mg/mL insulin, and 0.4% BSA) to allow sphere formation. Primary spheres were collected, disaggregated with trypsin, and distributed to 96-well ultra low attachment plated prior to TPIV® treatment. Bacteria were administered at an MOI of 1000 for two hours before addition of anti-biotic cocktail (penstrep, gentamycin, oflaxacin). Sphere formation was assessed after 10-14 days in culture. Representative sphere images were captured before (FIG. 5, left upper panels) or after the addition of trypan blue to identify dead cells (FIG. 5, left bottom panel). Relative spherogenesis was shown in the right panel of FIG. 5. The data clearly showed that Stat3 knockdown in cancer stem cells inhibits sphereogenesis, demonstrating that Stat3 is a key self-renewal factor of cancer stem cells.

Example 2

Identification of Compounds that Inhibit Stat3 Pathway Activity

Inhibition of Stat3 Transcription Activity.

Figure 6:
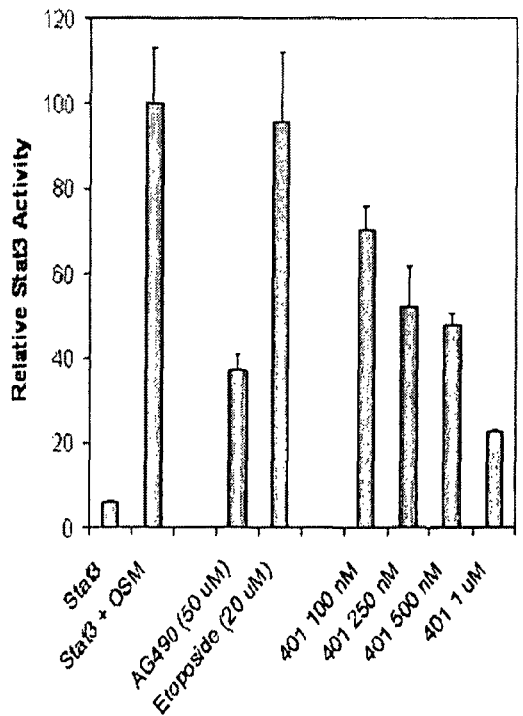
FIG. 6 shows that compound 401 inhibits Stat3 transcription activation activity.
Figure 6:
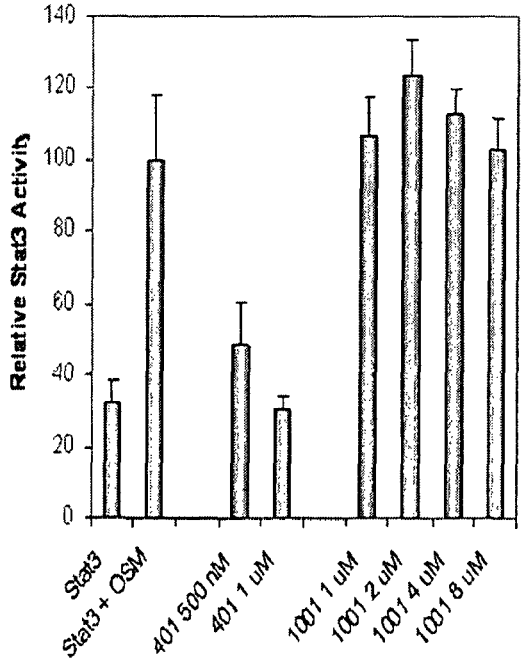

Compounds were tested for their ability to inhibit Stat3 transcription activation activity in cells using a Stat3-luciferase (Stat3-luc) reporter construct. Cells transfected with Stat3-luc were cultured in reduced serum medium prior to addition of indicated compound for 30 minutes. Cells were then stimulated with 25 ng/ml oncostatin M (OSM) for 6 hours followed by detection of Stat3-luc reporter activity. Incubation of cells with compound 401 inhibited OSM-stimulated Stat3 reporter activity (FIG. 6, left panel). AG490, a known inhibitor of the Jak-Stat pathway, was included as a positive control for Stat3 inhibition. Etoposide, included as a control for genotoxic activity, showed little or no Stat3 inhibition. Compound 1001, which is naphthalene instead of naphthoquinone as the compounds in this invention, did not inhibit OSM-stimulated Stat3 reporter activity even at a much higher concentration (FIG. 6, right panel).

Additional compounds were tested in the Stat3 luciferase reporter assays and the results are summarized in Table 3.

TABLE 3

| Compound # | IC$_{50}$ in Stat3-Luc assays |
| --- | --- |
| 401 | ~0.25 µM |
| 416 | ~0.75 µM |
| 418 | ~0.75 µM |
| 301 | ~2 µM |

Inhibition of Stat3 DNA-Binding Activity.

Figure 7A:
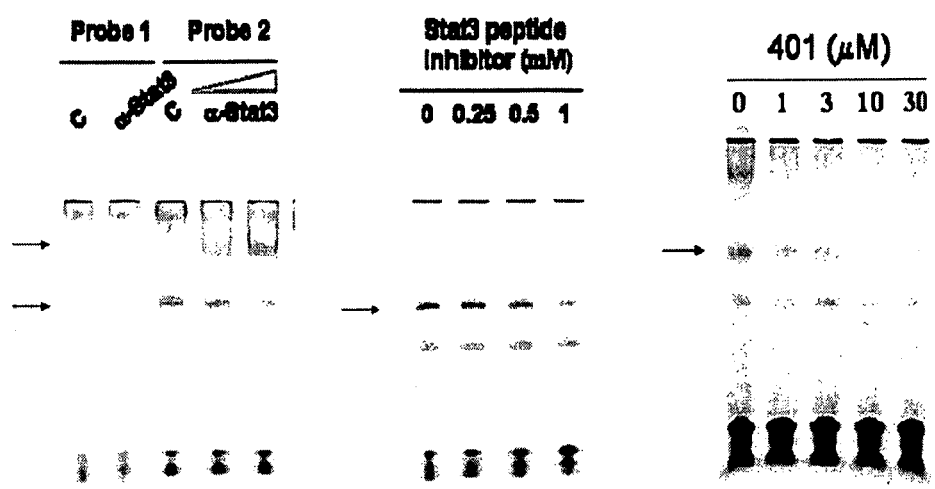
FIG. 7A shows that compound 401 inhibits Stat3 DNA-binding activity in nuclear extract.

Nuclear extracts from HeLa cells, which contain constitutively activated Stat3 as detected by phosphorylation at the tyrosine 705 residue, were used to perform Stat3 EMSAs to monitor Stat3 DNA binding activity. Nuclear extracts were incubated with indicated compound prior to incubation with IR700-labeled Stat3 consensus oligonucleotide. Binding of Stat3 to the oligonucleotide was monitored by gel electrophoresis and detection using a LiCor Odyssey infrared scanner. The Stat3 retarded band was identified and confirmed by supershift with the anti-Stat3 antibody (FIG. 7A, left panel) and dose-dependent inhibition with the Stat3 peptide (FIG. 7A, middle panel). Dose dependent inhibition of Stat3 DNA binding was observed following incubation of the labeled probe with compound 401 (FIG. 7A, right panel).

Figure 7B:
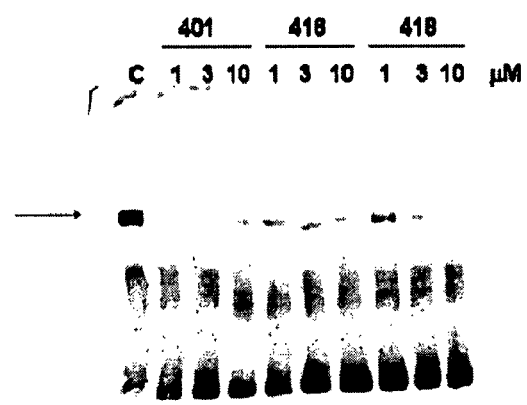
FIG. 7B shows that compounds 401, 416 and 418 inhibit Stat3 DNA-binding activity in nuclear extract.

Additional compounds were tested in the EMSA assays. As shown in FIG. 7B, compounds 401, 416 and 418 can inhibit Stat3's DNA binding activity.

Inhibition of Stat3 Downstream Effectors in Xenograft Tumor Tissues.

Figure 8:
FIG. 8A shows that compound 401 inhibits Stat3 DNA-binding activity in xenograft tumor tissues.
FIG. 8B shows that compound 401 inhibits the expression level of the Stat3 downstream effectors in xenograft tumor tissues.
Figure 8:
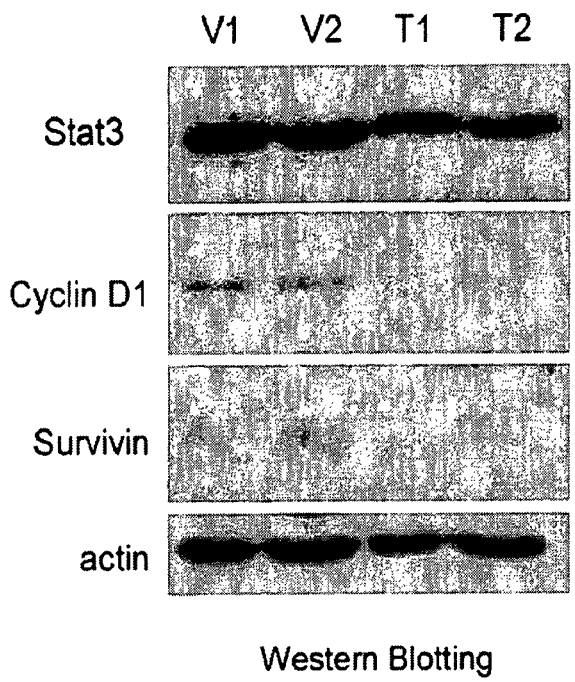

Extracts were prepared from xenografted Paca2 tumors that were treated with compound 401 or vehicle control 4 hours prior to harvest. The samples were analyzed by western blots and EMSA to evaluate the Stat3 downstream effector expression level and Stat3 DNA binding activity. Compound 401 treated sample (T) showed a decrease in Stat3 DNA binding activity over the control (V) (FIG. 8A). In addition, compound 401 treatment resulted in a decrease in the expression level of Stat3's downstream effectors cyclin D1 and survivin (FIG. 8B).

Example 3

Identification of Compounds that Target Cancer Stem Cells

Identification of Compounds that are Apoptotic to Cancer Stem Cells.

Figure 9A:
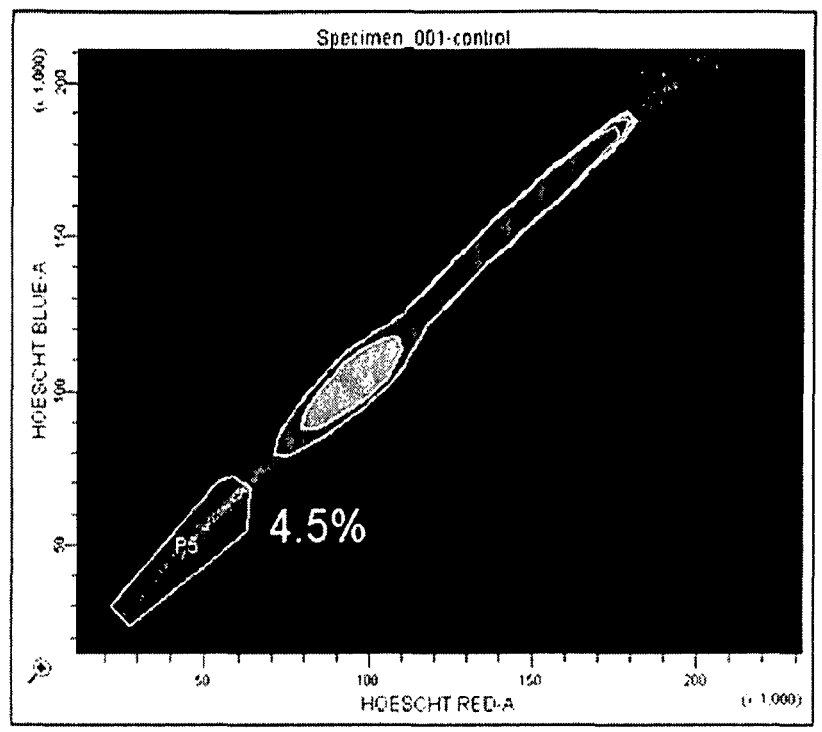
FIG. 9A shows the sorting and analysis of the Hoechst Side Population.
Figure 9A:
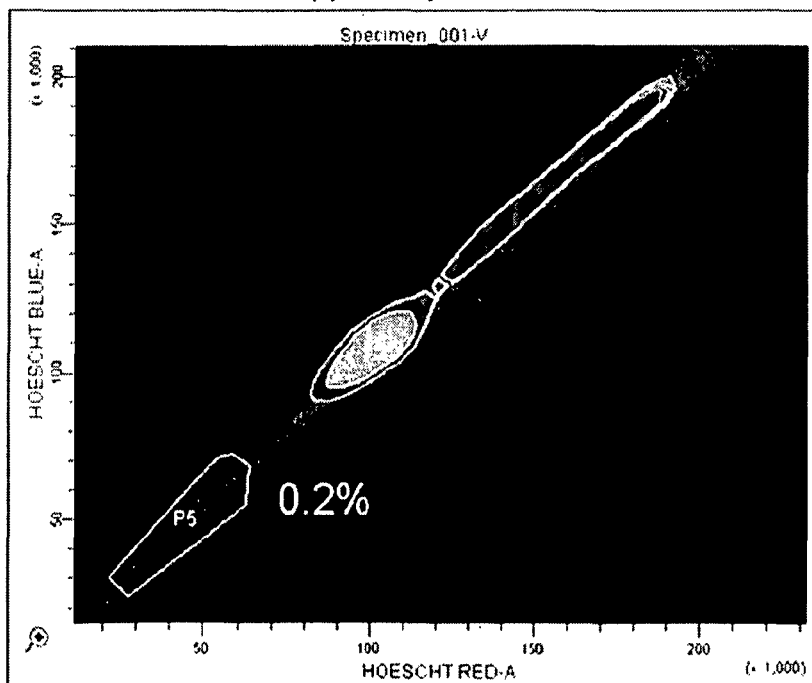

Since cancer stem cells have been demonstrated to actively efflux Hoechst, SW480 cells were stained with Hoechst and the side population (shown in FIG. 9A, left panel gated area) was sorted out to enrich the cancer stem cells. To confirm that this side population is enriched with cancer stem cells, a control set of SW480 cells were first treated with Verapamil, an inhibitor of ABC transporters, before stained with Hoechst. As shown in the right panel of FIG. 9A, Verapamil treatment results in the loss of the side population.

Figure 9B:
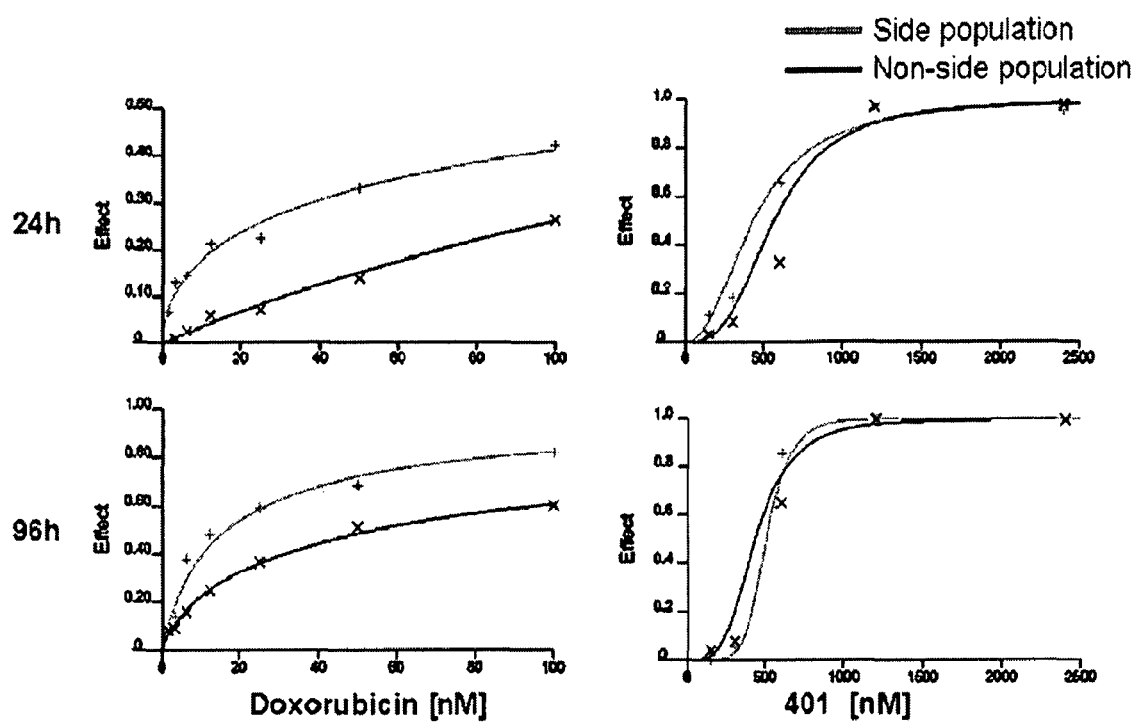
FIG. 9B shows that Hoechst Side Population is as sensitive as non-side population to compound 401.

The $IC_{50}$ of compound 401 against the Hoechst side population was accessed in MTT assays and was compared to the $IC_{50}$ against the non-side population. The results show that the side population is as sensitive as the non-side population to compound 401 (FIG. 9B, right panels). However, the side population is much more resistant than the non-side population to Doxorubicin (FIG. 9B, left panels), which is consistent with previous publications [7, 82]. These data suggest that compound 401 kills cancer stem cells.

Figure 10A:
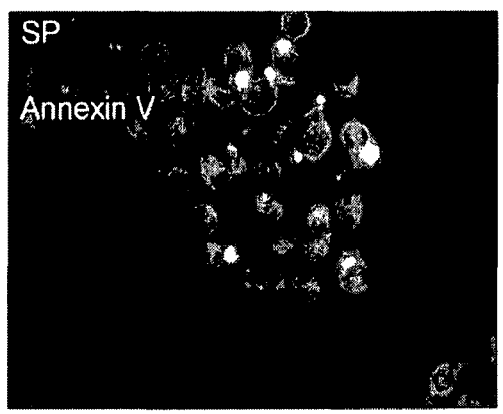
FIG. 10A shows that compound 401 is apoptotic to Hoechst Side Population cells.

The Hoechst side population cells were treated with compound 401 and the mode of cell death was accessed by Annexin V (an early marker for apoptosis) staining. The results show that the dying cells are Annexin V positive (FIG. 10A), demonstrating that compound 401 is apoptotic to cancer stem cells.

Figure 10B:
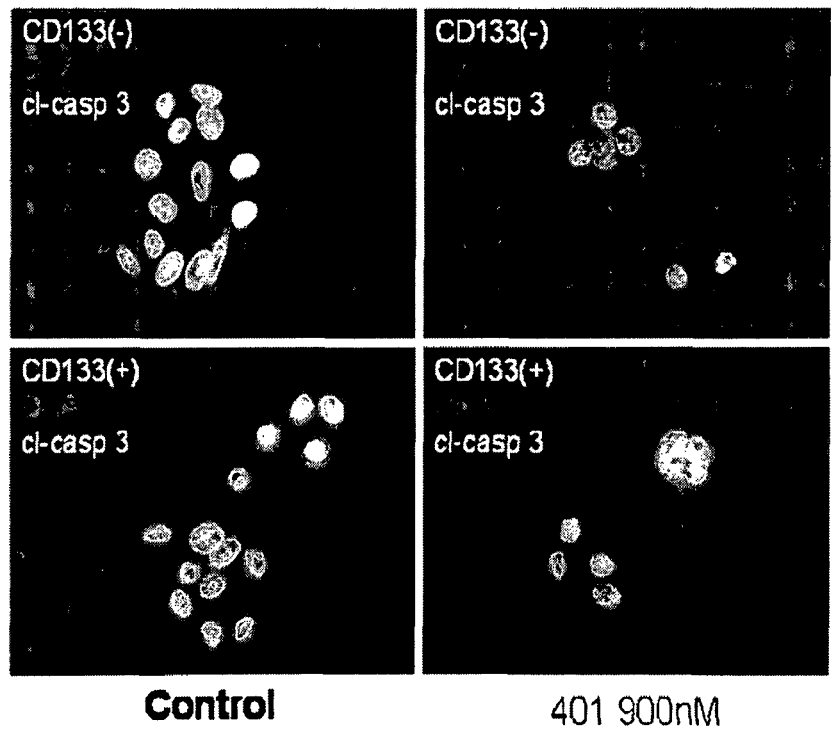
FIG. 10B shows that compound 401 is apoptotic to CD133$^+$ cells.

Alternatively, we performed CD133 (one of the common cancer stein cell surface markers) antibody magnetic beads pull down to enrich cancer stem cells. The $CD133^+$ cells were then treated with compound 401 followed by staining with antibody against cleaved-Caspase 3 (a hallmark of apoptosis). As shown in FIG. 10B, many of the $CD133^+$ cells become cleaved-Caspase 3 positive after compound 401 treatment, corroborating that compound 401 is apoptotic to cancer stem cells.

Identification of Compounds that Inhibit CSC Spherogenesis In Vitro.

Figure 11:
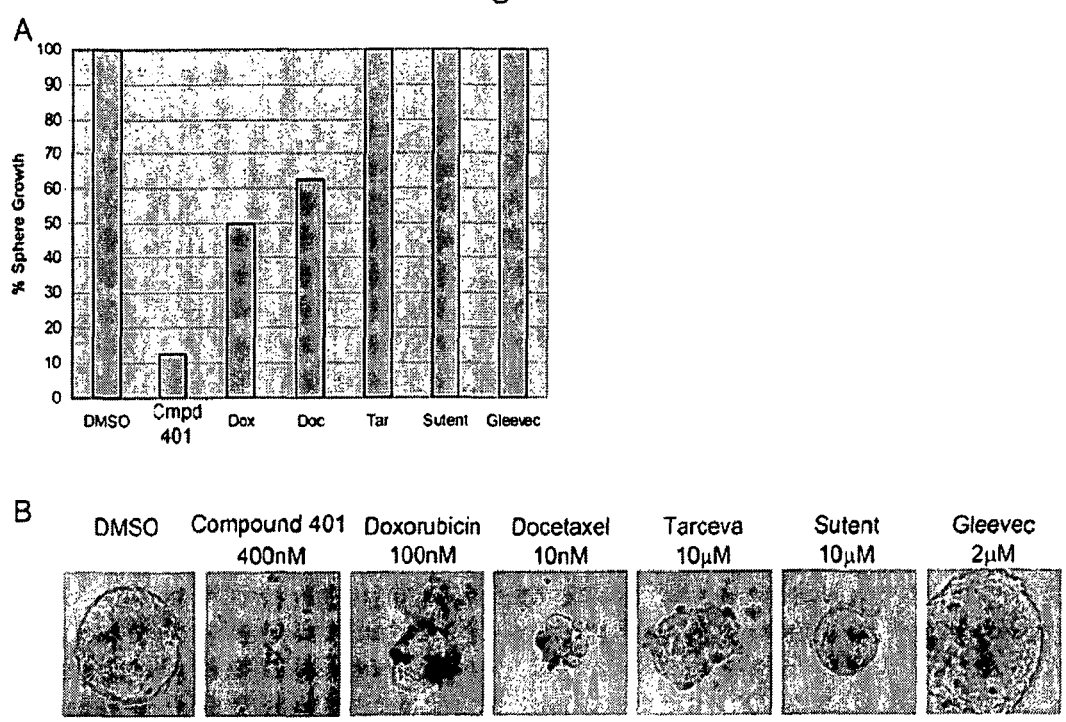
FIG. 11 shows that compound 401 blocks CD44$^{high}$ sphere formation.

One of the hallmarks of cancer stem cells is their ability to self-renew. A reliable method of measuring the self-renewal capacity of cell populations is the ability to be cultured as spheres in the absence of serum or attachment. To compare the ability of compound 401 to other targeted and chemotherapeutic agents, FACS-isolated $CD44^{high}$ CSCs were grown as spheres for 72 hours before being challenged with a panel of therapeutic agents. Of the agents tested, only compound 401 was effective at preventing sphere proliferation (FIG. 11). Note that spheres were resistant to doxorubicin and docetaxel despite being applied at approximately ten times their $IC_{50}$ concentrations for cell death in similar assays. Tarceva, Sutent, and Gleevec were added at approximately three times their reported therapeutic concentrations. This demonstrates that while cancer stem cells are resistant to conventional chemotherapeutic and targeted agents, compound 401 is highly effective at inhibiting their growth.

Identification of Compounds that Inhibit CSC Spherogenesis In Vivo.

Figure 12:
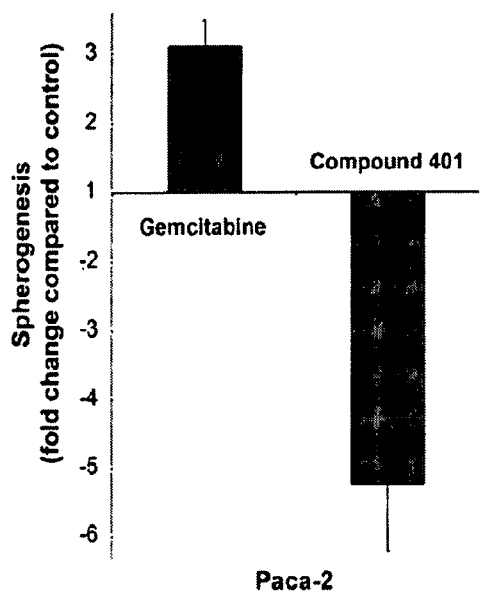
FIG. 12 shows that in vivo compound 401 treatment decreases the spherogenesis of the xenografted tumor cells.
Figure 12:
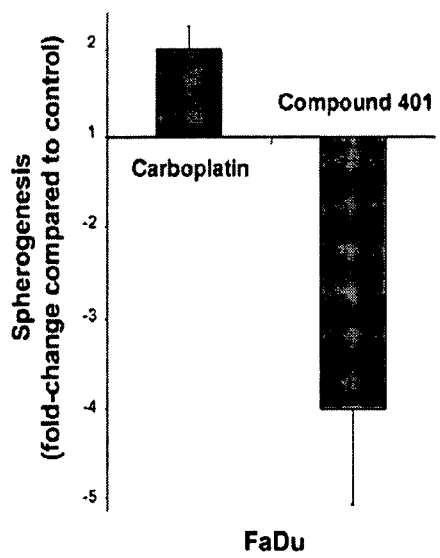

Six-week-old female athymic nu/nu mice were obtained from Charles River Labs (Wilmington, Mass.). Mice were injected subcutaneously on the flank with $6\times10^6$ FaDu or Paca2 cancer cells in 0.2 mL of serum-free DMEM. After xenografts reached ~200 mm³ in size, animals bearing Paca2 xenograft tumors were administered with either vehicle, gemcitabine (120 mg/kg, twice a week), or compound 401 (20 mg/kg) by ip for one week and animals bearing FaDu xenograft tumors were administered daily with either vehicle, carboplatin (30 mg/kg), or compound 401 (20 mg/kg) via ip for two weeks before sacrifice. Tumors were then collected for Paca2 and FaDu cells, respectively. Single cell suspensions were obtained following animal sacrifice, and sterile removal of tumors. Briefly, tumors were minced with sterile scalpels into 0.1 mm³ pieces before being digested in 1 mg/mL collagenase/HBSS for 15-30 minutes with constant agitation. Following passage through a 40 μm mesh filter, RBCs, dead cells, and cell debris were removed by layering the cell suspension onto 1 mL of Histopaque and collecting the interface layer after centrifugation at 1440×g for 30 minutes. Live cells were then counted and used to measure their ability to form spheres. Cells were distributed to ultra low attachment 96 well plates at a density of 100 cells per well in cancer stem cell media (DMEM/F12, B27 Neurobasal supplement, 20 ng/mL EGF, 10 ng/mL FGF, 4 μg/mL insulin, and 0.4% BSA). Fresh media was added every three days, and sphere formation was determined after 10-14 days in culture. Spheres with >50 cells were scored. At conclusion of experiment, trypan blue was added to identify dead cells. As shown in FIG. 12, standard chemotherapies gemcitabine (upper panel) and carboplatin (bottom panel) enriched cancer stem cells evidenced by the increased spherogenesis. In contrast, compound 401 treatments decreased cancer stem cells as is evident by the decreased spherogenesis.

Example 4

Anti-Metastasis Efficacy

Figure 13:
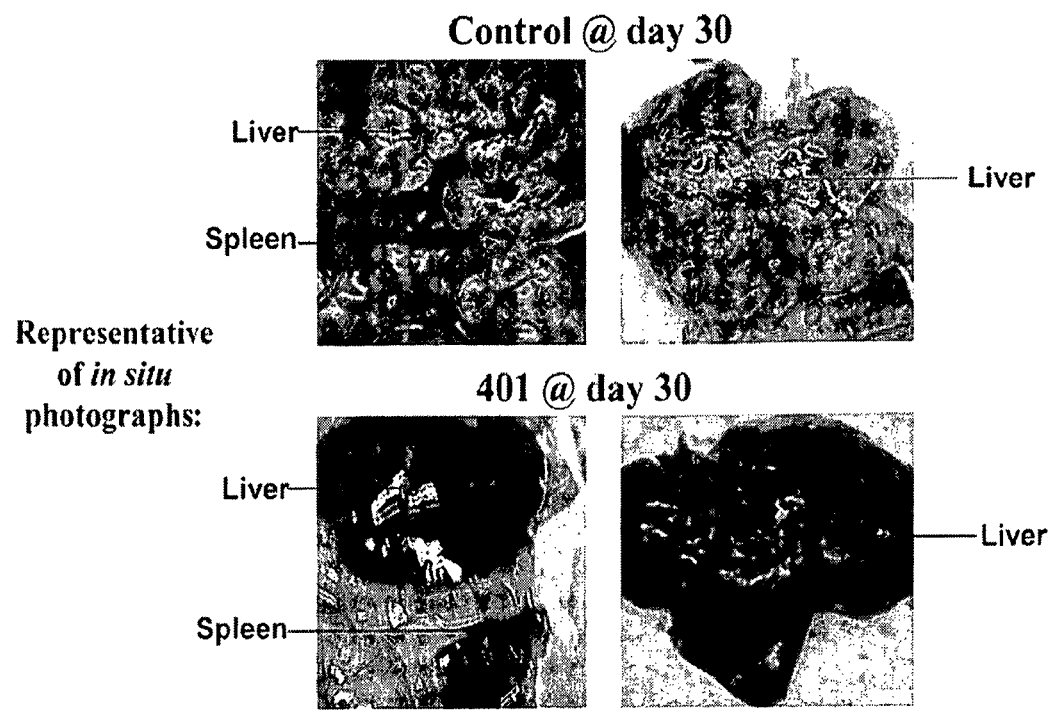
FIG. 13 shows that compound 401 inhibits metastasis in ISMS model.

Compound 401 was also tested for its capability to inhibit metastasis in ISMS model. The intrasplenic-nude mouse model system (ISMS model) is appropriate for studies of the malignant behavior of colorectal carcinomas, as this technique can produce experimental metastases in the liver. In this model, one million HT29 cells in 0.1 ml PBS were injected under the spleen capsule of the nude mice. The spleen was replaced in the peritoneal cavity and the incision was closed. Mice were sacrificed when moribund or 30 days after the injection. The spleen and liver were removed and examined, and the number of tumor lesions was recorded. Mice were divided into 2 groups, a control group given vehicle (n=4) and the other group receiving 20 mg/kg compound 401 (n=4). Drug was administered via ip. 5 days/week starting from day 2 to day 30 after i.s. injection. The numbers of primary tumors and metastatic liver tumors were estimated microscopically. Representative pictures are shown in FIG. 13. In the vehicle control group, there was heavy burden of primary tumors at spleen (FIG. 13, upper left panel). Massive spontaneous liver metastases were also observed (FIG. 13, upper right panel). Compound 401 treatments significantly reduced the number of primary tumor foci and the spontaneous liver metastasis (FIG. 13, lower panels).

Example 5

Combinatorial Activity

Paca2 human pancreatic cancer cells, A549 human lung cancer cells, and HepG2 human liver cancer cells (American Type Culture Collection) were cultured in Dulbecco's modified Eagle's medium containing 10% fetal bovine serum, 100 units/mL penicillin, 100 µg/mL streptomycin, and 2 mM L-glutamine. Compound 401 and Sutent were synthesized by Boston Biomedical, Inc. Carboplatin, doxorubicin, docetaxel, etoposide were obtained from Sigma (St. Louis, Mo.) and dissolved in water or DMSO at 10 mM. Erlotinib was from American Custom Chemicals (San Diego, Calif.). Gemcitabine was from Eli Lilly (Indianapolis, Ind.) in an aqueous 20 mM stock solution. Sorafenib was purchased from LKT (St. Paul, Minn.). Lapatinib was from LC Laboratories (Woburn, Mass.). Unless otherwise noted all compounds were solubilized in DMSO at 10 mM and aliquoted at −20° C. Exponentially growing Paca2 pancreatic cancer cells were seeded at 1,000 cells per well in 6-well plates and allowed to attach for 24 hours. Increasing concentrations of individual drugs and those in combination were then added to the media for another 24 hours. After 24 hours exposure, the drug was removed and fresh media was added for the next 10-14 days, allowing for colony formation. Cells were fixed and stained with GIEMSA (Gibco BRL). Colonies of greater than 50 cells were scored as survivors and percentage of cell survival was normalized to untreated controls. Results are an average of duplicate experiments. Alternatively, MTT assays were performed 72 hours post-treatment in A549 and HepG2 cells.

Figure 14:
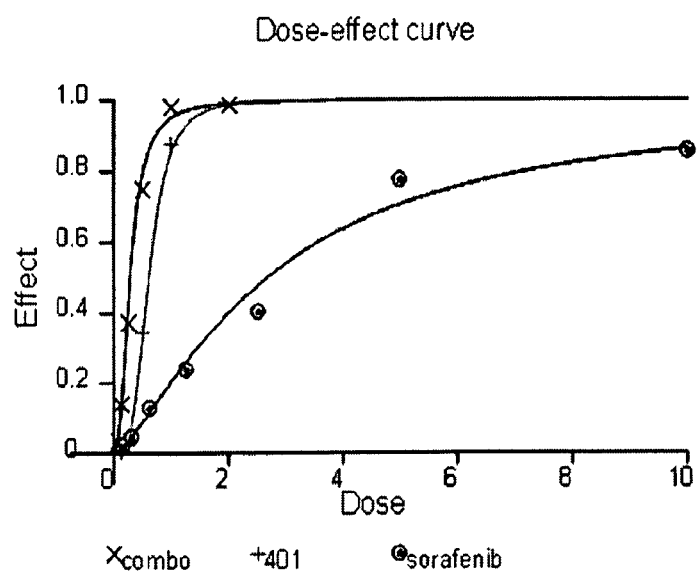
FIG. 14 shows that compound 401 has a synergistic effect with sorafenib in A549 human lung cancer cells.
Figure 15:
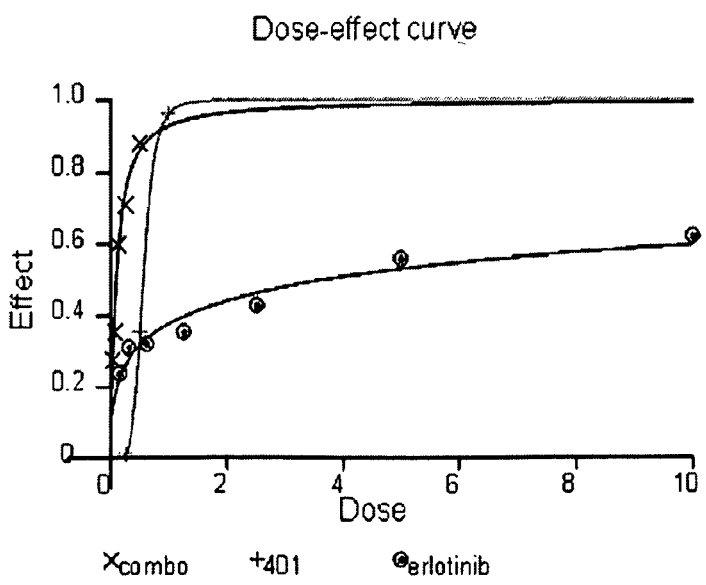
FIG. 15 shows that compound 401 has a synergistic effect with erlotinib in A549 human lung cancer cells.
Figure 16:
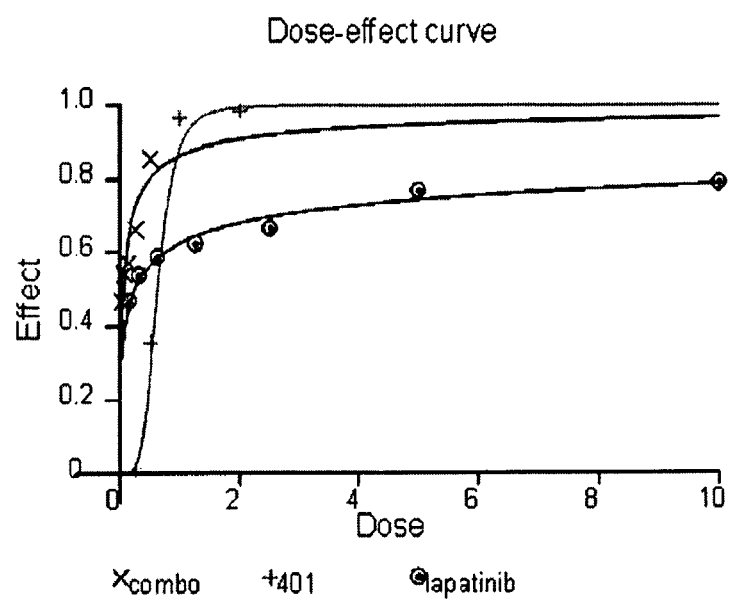
FIG. 16 shows that compound 401 has a synergistic effect with lapatinib in A549 human lung cancer cells.
Figure 17:
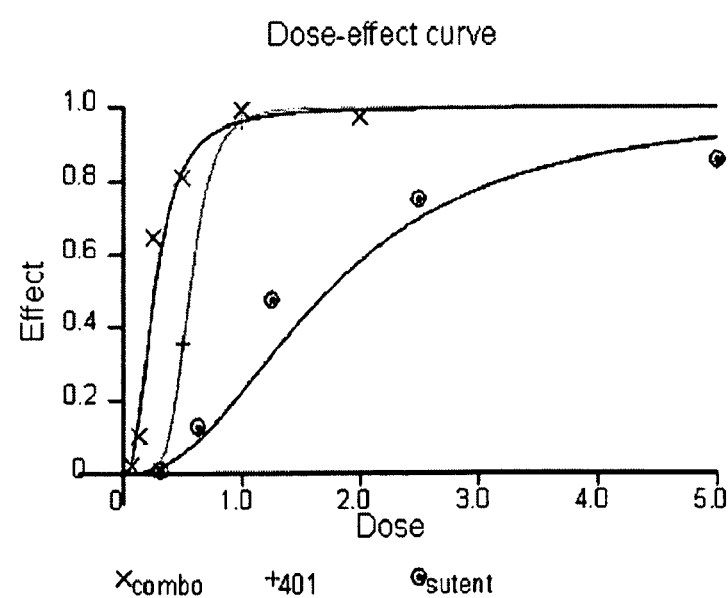
FIG. 17 shows that compound 401 has a synergistic effect with sutent in A549 human lung cancer cells.

Our data demonstrate that compound 401 has beneficial effects when combined with all the drugs tested. Among them, combination with tyrosine kinase inhibitors (TKI) showed most remarkable results. For examples, as shown in FIG. 14, compound 401 has a synergistic effect in combination with sorafenib in human lung A549 cells at 72 hours. Similarly, FIGS. 15 to 17 show that compound 401 also has synergistic effects in combination with erlotinib, lapatinib, and sunitinib (Sutent®), respectively, in human lung A549 cells at 72 hours. The rest of the data are summarized in Table 4 and demonstrate that compound 401 showed beneficial effects when combined with all the drugs tested.

TABLE 4

| Compound 401 (% Inhibition) | X (% Inhibition) | Compound 401 + X (% Inhibition) | Combo drug (X) | Exemplary function |
|---|---|---|---|---|
| 7 day colony formation PACA2 cells | | | | |
| 32 [66 nM] | — | — | — | |
| 66 [133 nM] | — | — | — | |
| 32 | 43 [16 µM] | 80 | Carboplatin | DNA alkylating agent, DNA damaging |
| 32 | 89 [16 nM] | 100 | Doxorubicin | DNA-intercalator, antibiotic, DNA damaging |
| 32 | 48 [0.33 nM] | 62 | Docetaxel | Anti-mitotic |
| 32 | 58 [660 nM] | 81 | Etoposide | topoisomerase II inhibitor, DNA damaging |
| 32 | 27 [6.75 µM] | 74 | Lapatinib | TKI |
| 32 | 26 [16 µM] | 40 | Erlotinib | TKI |
| 32 | 52 [12 µM] | 73 | Sunitinib | TKI |
| 66 | 36 [33 µM] | 96 | Gemcitabine | Anti-metabolite |
| 66 | 66 [2 µM] | 100 | Sorafenib | TKI |
| 72 hour MTT A549 cells | | | | |
| 35 [500 nM] | 43 [2.5 µM] | 88 | Erlotinib | TKI |
| 36 [250 nM] | 29 [12.5 nM] | 54 | Doxorubicin | DNA-intercalator, antibiotic, DNA damaging |
| 35 [500 nM] | 75 [2.5 µM] | 81 | Sunitinib | TKI |
| 35 [500 nM] | 40 [2.5 µM] | 74 | Sorafenib | TKI |
| 35 [500 nM] | 66 [2.5 µM] | 85 | Lapatinib | TKI |
| 72 hour MTT HepG2 cells | | | | |
| 43 [250 nM] | 23 [12.5 µM] | 72 | Doxorubicin | DNA-intercalator, antibiotic, DNA damaging |
| 43 | 51 [2.5 µM] | 68 | Sorafenib | TKI |
| 7 [125 nM] | 34 [625 nM] | 42 | Sorafenib | TKI |

Furthermore, we tested the combo effect of compound 401 with gemcitabine in human pancreatic cancer xenograft model. Briefly, athymic female nude mice (Ncr) were inoculated subcutaneously with $8 \times 10^6$ MIA PaCa-2 human pancreatic cancer cells, and the tumors were allowed to grow to approximately 150 mm$^3$ in size. The animals were randomized into four groups of six animals per group, and were treated with vehicle control, compound 401 at 100 mg/kg in the clinical formulation (20% Gelucire) orally daily, gemcitabine (Gemzar®) at 120 mg/kg (in PBS) intraperitoneally every three days, or both. The mice received a total of two-week treatments, and the mean volumes of the tumors were analyzed.

Figure 18:
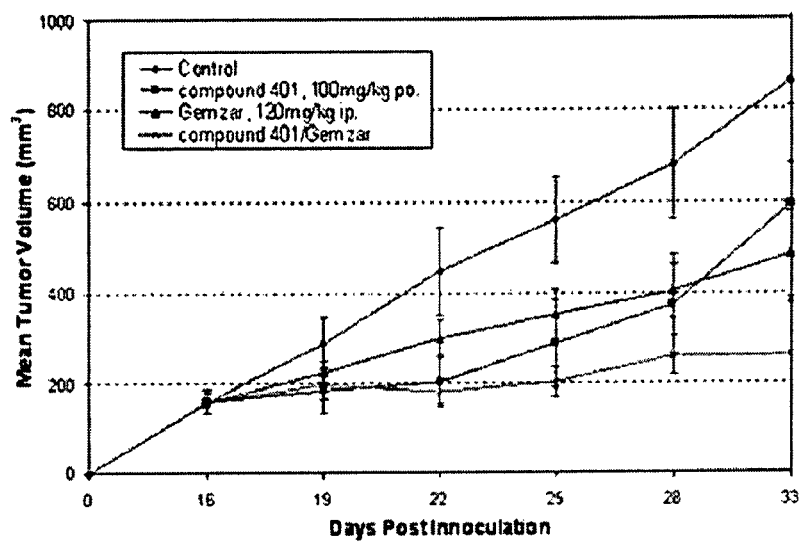
FIG. 18 shows that compound 401 has a synergistic effect with gemcitabine in Paca-2 human pancreatic xenograft model.

As shown in FIG. 18, treatment with either compound 401 (100 mg/kg) or gemcitabine (120 mg/kg) alone retarded tumor growth to a similar extent during the treatment. Animals treated with compound 401 (100 mg/kg) in combination with gemcitabine (120 mg/kg) showed a synergistic effect on tumor growth. No significant toxicity was noted for any of the treatment regimens. Our data suggest that compound 401 in combination with gemcitabine is clinically beneficial in treating pancreatic cancer All references cited herein are incorporated herein by reference in their entirety to the extent allowed by applicable laws and for all purposes to the same extent as if each individual publication or patent or patent application is specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, reaction conditions, analytical results and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

REFERENCES

1. Bonnet, D., *Normal and leukaemic stem cells*. Br J Haematol, 2005. 130(4): p. 469-79.
2. Bonnet, D. and J. E. Dick, *Human acute myeloid leukemia is organized as a hierarchy that originates from a primitive hematopoietic cell*. Nat Med, 1997. 3(7): p. 730-7.
3. Baumann, M., M. Krause, and R. Hill, *Exploring the role of cancer stem cells in radioresistance*. Nat Rev Cancer, 2008. 8(7): p. 545-54.
4. Hambardzumyan, D., M. Squatrito, and E. C. Holland, *Radiation resistance and stem-like cells in brain tumors*. Cancer Cell, 2006. 10(6): p. 454-6.
5. Dean, M., T. Fojo, and S. Bates, *Tumour stem cells and drug resistance*. Nat Rev Cancer, 2005. 5(4): p. 275-84.
6. Jones, R. J., W. H. Matsui, and B. D. Smith, *Cancer stem cells: are we missing the target?* J Natl Cancer Inst, 2004. 96(8): p. 583-5.
7. Ho, M. M., et al., *Side population in human lung cancer cell lines and tumors is enriched with stem-like cancer cells*. Cancer Res, 2007. 67(10): p. 4827-33.
8. Wang, J., et al., *Identification of cancer stem cell-like side population cells in human nasopharyngeal carcinoma cell line*. Cancer Res, 2007. 67(8): p. 3716-24.
9. Haraguchi, N., et al., *Characterization of a side population of cancer cells from human gastrointestinal system*. Stem Cells, 2006. 24(3): p. 506-13.
10. Doyle, L. A. and D. D. Ross, *Multidrug resistance mediated by the breast cancer resistance protein BCRP (ABCG2)*. Oncogene, 2003. 22(47): p. 7340-58.
11. Alvi, A. J., et al., *Functional and molecular characterisation of mammary side population cells*. Breast Cancer Res, 2003. 5(1): p. R1-8.
12. Frank, N. Y., et al., *ABCB5-mediated doxorubicin transport and chemoresistance in human malignant melanoma*. Cancer Res, 2005. 65(10): p. 4320-33.
13. Schatton, T., et al., *Identification of cells initiating human melanomas*. Nature, 2008. 451(7176): p. 345-9.
14. Kondo, T., T. Setoguchi, and T. Taga, *Persistence of a small subpopulation of cancer stem-like cells in the C6 glioma cell line*. Proc Natl Acad Sci USA, 2004. 101(3): p. 781-6.
15. Goodell, M. A., et al., *Isolation and functional properties of murine hematopoietic stem cells that are replicating in vivo*. J Exp Med, 1996. 183(4): p. 1797-806.
16. Al-Hajj, M., et al., *Prospective identification of tumorigenic breast cancer cells*. Proc Natl Acad Sci USA, 2003. 100(7): p. 3983-8.
17. Collins, A. T., et al., *Prospective identification of tumorigenic prostate cancer stem cells*. Cancer Res, 2005. 65(23): p. 10946-51.
18. Li, C., et al., *Identification of pancreatic cancer stem cells*. Cancer Res, 2007. 67(3): p. 1030-7.
19. Ma, S., et al., *Identification and characterization of tumorigenic liver cancer stem/progenitor cells*. Gastroenterology, 2007. 132(7): p. 2542-56.
20. Prince, M. E., et al., *Identification of a subpopulation of cells with cancer stem cell properties in head and neck squamous cell carcinoma*. Proc Natl Acad Sci USA, 2007. 104(3): p. 973-8.
21. Ricci-Vitiani, L., et al., *Identification and expansion of human colon-cancer-initiating cells*. Nature, 2007. 445 (7123): p. 111-5.
22. Singh, S. K., et al., *Identification of a cancer stem cell in human brain tumors*. Cancer Res, 2003. 63(18): p. 5821-8.
23. Dalerba, P., et al., *Phenotypic characterization of human colorectal cancer stem cells*. Proc Natl Acad Sci USA, 2007. 104(24): p. 10158-63.
24. Klein, W. M., et al., *Increased expression of stem cell markers in malignant melanoma*. Mod Pathol, 2007. 20(1): p. 102-7.
25. Yu, H. *Stat3: Linking oncogenesis with tumor immune evasion*. in *AACR 2008 Annual Meeting*. 2008. San Diego, Calif.
26. Pedranzini, L., A. Leitch, and J. Bromberg, *Stat3 is required for the development of skin cancer*. J Clin Invest, 2004. 114(5): p. 619-22.
27. Catlett-Falcone, R., et al., *Constitutive activation of Stat3 signaling confers resistance to apoptosis in human U266 myeloma cells*. Immunity, 1999. 10(1): p. 105-15.
28. Bromberg, J. F., et al., *Stat3 as an oncogene*. Cell, 1999. 98(3): p. 295-303,
29. Kanda, N., et al., *STAT3 is constitutively activated and supports cell survival in association with survivin expression in gastric cancer cells*. Oncogene, 2004. 23(28): p. 4921-9.

30. Schlette, E. J., et al., *Survivin expression predicts poorer prognosis in anaplastic large-cell lymphoma.* J Clin Oncol, 2004. 22(9): p. 1682-8.
31. Niu, G., et al., *Constitutive Stat3 activity up-regulates VEGF expression and tumor angiogenesis.* Oncogene, 2002. 21(13): p. 2000-8.
32. Xie, T. X., et al., *Stat3 activation regulates the expression of matrix metalloproteinase-2 and tumor invasion and metastasis.* Oncogene, 2004. 23(20): p. 3550-60.
33. Kortylewski, M., et al., *Inhibiting Stat3 signaling in the hematopoietic system elicits multicomponent antitumor immunity.* Nat Med, 2005. 11(12): p. 1314-21.
34. Burdelya, L., et al., *Stat3 activity in melanoma cells affects migration of immune effector cells and nitric oxide-mediated antitumor effects.* J Immunol, 2005. 174(7): p. 3925-31.
35. Wang, T., et al., *Regulation of the innate and adaptive immune responses by Stat-3 signaling in tumor cells.* Nat Med, 2004. 10(1): p. 48-54.
36. Darnell, J. E., *Validating Stat3 in cancer therapy.* Nat Med, 2005. 11(6): p. 595-6.
37. Zhang, L., et al., *Intratumoral delivery and suppression of prostate tumor growth by attenuated Salmonella enterica serovar typhimurium carrying plasmid-based small interfering RNAs.* Cancer Res, 2007. 67(12): p. 5859-64.
38. Campbell, I. L., *Cytokine-mediated inflammation, tumorigenesis, and disease-associated JAK/STAT/SOCS signaling circuits in the CNS.* Brain Res Brain Res Rev, 2005. 48(2): p. 166-77.
39. Harris, T. J., et al., *Cutting edge: An in vivo requirement for STAT3 signaling in TH17 development and TH17-dependent autoimmunity.* J Immunol, 2007. 179(7): p. 4313-7.
40. Watson, C. J. and W. R. Miller, *Elevated levels of members of the STAT family of transcription factors in breast carcinoma nuclear extracts.* Br J Cancer, 1995. 71(4): p. 840-4.
41. Song, J. I. and J. R. Grandis, *STAT signaling in head and neck cancer.* Oncogene, 2000. 19(21): p. 2489-95.
42. Song, L., et al., *Activation of Stat3 by receptor tyrosine kinases and cytokines regulates survival in human non-small cell carcinoma cells.* Oncogene, 2003. 22(27): p. 4150-65.
43. Savarese, T. M., et al., *Coexpression of oncostatin M and its receptors and evidence for STAT3 activation in human ovarian carcinomas.* Cytokine, 2002. 17(6): p. 324-34.
44. Toyonaga, T., et al., *Blockade of constitutively activated Janus kinase/signal transducer and activator of transcription-3 pathway inhibits growth of human pancreatic cancer.* Cancer Lett, 2003. 201(1): p. 107-16.
45. Corvinus, F. M., et al., *Persistent STAT3 activation in colon cancer is associated with enhanced cell proliferation and tumor growth.* Neoplasia, 2005. 7(6): p. 545-55.
46. Gao, B., et al., *Constitutive activation of JAK-STAT3 signaling by BRCA1 in human prostate cancer cells.* FEBS Lett, 2001. 488(3): p. 179-84.
47. Buettner, R., L. B. Mora, and R. Jove, *Activated STAT signaling in human tumors provides novel molecular targets for therapeutic intervention.* Clin Cancer Res, 2002. 8(4): p. 945-54.
48. Carson, W. E., *Interferon-alpha-induced activation of signal transducer and activator of transcription proteins in malignant melanoma.* Clin Cancer Res, 1998. 4(9): p. 2219-28.
49. Chen, C. L., et al., *Stat3 activation in human endometrial and cervical cancers.* Br Cancer, 2007. 96(4): p. 591-9.
50. Lai, R., et al., *STAT3 is activated in a subset of the Ewing sarcoma family of tumours.* J Pathol, 2006. 208(5): p. 624-32.
51. Punjabi, A. S., et al., *Persistent activation of STAT3 by latent Kaposi's sarcoma-associated herpesvirus infection of endothelial cells.* J Virol, 2007. 81(5): p. 2449-58.
52. Schaefer, L. K., et al., *Constitutive activation of Stat3alpha in brain tumors: localization to tumor endothelial cells and activation by the endothelial tyrosine kinase receptor (VEGFR-2).* Oncogene, 2002. 21(13): p. 2058-65.
53. Puthier, D., R. Bataille, and M. Amiot, *IL-6 up-regulates mcl-1 in human myeloma cells through JAK/STAT rather than ras/MAP kinase pathway.* Eur J Immunol, 1999. 29(12): p. 3945-50.
54. Migone, T. S., et al., *Constitutively activated Jak-STAT pathway in T cells transformed with HTLV-I.* Science, 1995. 269(5220): p. 79-81.
55. Spiekermann, K., et al., *Constitutive activation of STAT transcription factors in acute myelogenous leukemia.* Eur J Haematol, 2001. 67(2): p. 63-71.
56. Epling-Burnette, P. K., et al., *Inhibition of STAT3 signaling leads to apoptosis of leukemic large granular lymphocytes and decreased Mcl-1 expression.* J Clin Invest, 2001. 107(3): p. 351-62.
57. Weber-Nordt, R. M., et al., *Constitutive activation of STAT proteins in primary lymphoid and myeloid leukemia cells and in Epstein-Barr virus (EBV)-related lymphoma cell lines.* Blood, 1996. 88(3): p. 809-16.
58. Sommer, V. H., et al., *In vivo activation of STAT3 in cutaneous T-cell lymphoma. Evidence for an antiapoptotic function of STAT3.* Leukemia, 2004. 18(7): p. 1288-95.
59. Lai, R., et al., *Signal transducer and activator of transcription-3 activation contributes to high tissue inhibitor of metalloproteinase-1 expression in anaplastic lymphoma kinase-positive anaplastic large cell lymphoma.* Am J Pathol, 2004. 164(6): p. 2251-8.
60. Fu, X. Y., *STAT3 in immune responses and inflammatory bowel diseases.* Cell Res, 2006. 16(2): p. 214-9.
61. Feldmann, M., F. M. Brennan, and R. N. Maini, *Role of cytokines in rheumatoid arthritis.* Annu Rev Immunol, 1996. 14: p. 397-440.
62. Krause, A., et al., *Rheumatoid arthritis synoviocyte survival is dependent on Stat3.* J Immunol, 2002. 169(11): p. 6610-6.
63. Pfitzner, E., et al., *The role of STATs in inflammation and inflammatory diseases.* Curr Pharm Des, 2004. 10(23): p. 2839-50.
64. Lovato, P., et al., *Constitutive STAT3 activation in intestinal T cells from patients with Crohn's disease.* J Biol Chem, 2003. 278(19): p. 16777-81.
65. Ishihara, K. and T. Hirano, *IL-6 in autoimmune disease and chronic inflammatory proliferative disease.* Cytokine Growth Factor Rev, 2002. 13(4-5): p. 357-68.
66. Ivashkiv, L. B. and I. Tassiulas, *Can SOCS make arthritis better?* J Clin Invest, 2003. 111(6): p. 795-7.
67. Sengupta, T. K., et al., *Activation of monocyte effector genes and STAT family transcription factors by inflammatory synovial fluid is independent of interferon gamma.* J Exp Med, 1995. 181(3): p. 1015-25.
68. Shouda, T., et al., *Induction of the cytokine signal regulator SOCS3/CIS3 as a therapeutic strategy for treating inflammatory arthritis.* J Clin Invest, 2001. 108(12): p. 1781-8.

69. Harada, T., et al., *Increased expression of STAT3 in SLE T cells contributes to enhanced chemokine-mediated cell migration.* Autoimmunity, 2007. 40(1): p. 1-8.
70. Simeone-Penney, M. C., et al., *Airway epithelial STAT3 is required for allergic inflammation in a murine model of asthma.* J Immunol, 2007. 178(10): p. 6191-9.
71. Hagler, M., Smith-Norowitz, T., Chice, S., Wallner, S., Viterbo, D., Mueller, C., Groos, R., Nowakowski, M., Schulze, R., Zenilman, M., *Sophorolipids decrease IgE production in U266 cells by downregulation of BSAP (Pax5), TLR-2, STAT3 and IL-6.* Journal of Allergy and Clinical Immunology, 2007. 119(S1): p. S263-S263.
72. Benkhart, E. M., et al., *Role of Stat3 in lipopolysaccharide-induced IL-10 gene expression.* J Immunol, 2000. 165(3): p. 1612-7.
73. Sano, S., et al., *Stat3 links activated keratinocytes and immunocytes required for development of psoriasis in a novel transgenic mouse model.* Nat Med, 2005. 11(1): p. 43-9.
74. Lim, C. P., et al., *Stat3 contributes to keloid pathogenesis via promoting collagen production, cell proliferation and migration.* Oncogene, 2006. 25(39): p. 5416-25.
75. Arany, I., et al., *Correlation between pretreatment levels of interferon response genes and clinical responses to an immune response modifier (Imiquimod) in genital warts.* Antimicrob Agents Chemother, 2000. 44(7): p. 1869-73.
76. Tefferi, A., *Classification, diagnosis and management of myeloproliferative disorders in the JAK2V617F era.* Hematology Am Sac Hematol Educ Program, 2006: p. 240-5.
77. Roder, S., et al., *STAT3 is constitutively active in some patients with Polycythemia rubra vera.* Exp Hematol, 2001. 29(6): p. 694-702.
78. Kim, O, S., et al., *JAK-STAT signaling mediates gangliosides-induced inflammatory responses in brain microglial cells.* J Biol Chem, 2002. 277(43): p. 40594-601.
79. Wyss-Coray, T., *Inflammation in Alzheimer disease: driving force, bystander or beneficial response?* Nat Med, 2006. 12(9): p. 1005-15.
80. Stelmasiak, Z., et al., *Interleukin-6 concentration in serum and cerebrospinal fluid in multiple sclerosis patients.* Med Sci Monit, 2000. 6(6): p. 1104-8.
81. Ponti, D., et al., *Isolation and in vitro propagation of tumorigenic breast cancer cells with stem/progenitor cell properties.* Cancer Res, 2005. 65(13): p. 5506-11.
82. Szotek, P. P., et al., *Ovarian cancer side population defines cells with stem cell-like characteristics and Mullerian Inhibiting Substance responsiveness.* Proc Natl Acad Sci USA, 2006. 103(30): p. 11154-9.

The invention claimed is:

1. A method for treating cancer in a human subject in need thereof comprising administering
a composition comprising a therapeutically effective amount of at least one first agent chosen from 2-acetylnaphtho[2,3-b]furan-4,9-dione and pharmaceutically acceptable solvates thereof,
wherein said 2-acetylnaphtho[2,3-b]furan-4,9-dione is synthetic and
a composition comprising a therapeutically effective amount of at least one second agent chosen from growth factor-targeting agents, kinase-targeting agents, angiogenesis inhibitors, DNA-damaging agents, antimitotic agents, and antimetabolite agents,
wherein said cancer is head and neck cancer, brain cancer, breast cancer, lung cancer, liver cancer, pancreatic cancer, ovarian cancer, cervical cancer, uterine cancer, gastrointestinal cancer, kidney cancer, bladder cancer, vulval cancer, cancer of the peritoneum, prostate cancer, thyroid cancer, sarcomas, squamous cell cancer, melanoma, leukemia, lymphoma, or myeloma, wherein said cancer expresses activated STAT3.

2. The method of claim 1, wherein the cancer is metastatic.

3. The method of claim 1, wherein the cancer is refractory to chemotherapy or radiotherapy.

4. The method of claim 1, wherein the cancer is resistant to chemotherapy.

5. The method of claim 1, wherein the cancer has relapsed.

6. The method of claim 1, wherein said cancer is head and neck cancer.

7. The method of claim 6, wherein said head and neck cancer is salivary gland cancer.

8. The method of claim 1, wherein said cancer is brain cancer.

9. The method of claim 8, wherein said brain cancer is glioblastoma.

10. The method of claim 1, wherein said cancer is breast cancer.

11. The method of claim 1, wherein said cancer is lung cancer.

12. The method of claim 11, wherein said lung cancer is small-cell lung cancer, non-small-cell lung cancer, adenocarcinoma of the lung, and/or squamous carcinoma of the lung.

13. The method of claim 1, wherein said cancer is liver cancer.

14. The method of claim 13, wherein said liver cancer is a hepatocellular carcinoma.

15. The method of claim 1, wherein said cancer is pancreatic cancer.

16. The method of claim 1, wherein said cancer is ovarian cancer.

17. The method of claim 1, wherein said cancer is uterine cancer.

18. The method of claim 1, wherein said uterine cancer is endometrial cancer.

19. The method of claim 1, wherein said cancer is cervical cancer.

20. The method of claim 1, wherein said cancer is gastrointestinal cancer.

21. The method of claim 20, wherein said gastrointestinal cancer is esophageal cancer, gastroesophageal junction cancer, gastric cancer, colon cancer, and/or colorectal cancer.

22. The method of claim 20, wherein said gastrointestinal cancer is esophageal and/or gastroesophageal junction cancer.

23. The method of claim 20, wherein said gastrointestinal cancer is gastric cancer.

24. The method of claim 20, wherein said gastrointestinal cancer is colon cancer.

25. The method of claim 20, wherein said gastrointestinal cancer is colorectal cancer.

26. The method of claim 1, wherein said cancer is cancer of the peritoneum.

27. The method of claim 1, wherein said cancer is kidney cancer.

28. The method of claim 27, wherein said kidney cancer is renal cell carcinoma.

29. The method of claim 1, wherein said cancer is bladder cancer.

30. The method of claim 1, wherein said cancer is vulval cancer.

31. The method of claim 1, wherein said cancer is prostate cancer.

32. The method of claim 1, wherein said cancer is thyroid cancer.

33. The method of claim 1, wherein said cancer is a sarcoma.

34. The method of claim 1, wherein said cancer is squamous cell cancer.

35. The method of claim 1, wherein said cancer is melanoma.

36. The method of claim 1, wherein said cancer is leukemia.

37. The method of claim 1, wherein said cancer is lymphoma.

38. The method of claim 1, wherein said cancer is myeloma.

39. The method of claim 38, wherein said myeloma is multiple myeloma.

40. The method of claim 1, wherein said at least one second agent is chosen from bevacizurnab, bortezomib, capecitabine, cetuximab, fluorouracil, imatinib, irinotecan, leucovorin, oxaliplatin, panitumumab, pemetrexed, temozolomide, cisplatin, paclitaxel, erlotinib, sunitinib, lapatinib, sorafenib, carboplatin, doxorubicin, docetaxel, gemcitabine, and etoposide.

41. The method of claim 1, wherein said at least one second agent is chosen from growth factor-targeting agents.

42. The method of claim 1, wherein said at least one second agent is chosen from Epidermal Growth Factor Receptor-targeting agents and Vascular Endothelial Growth Factor Receptor-targeting agents.

43. The method of claim 1, wherein said at least one second agent is chosen from gefitinib, PD153035, cetuximab, bevacizumab, panitumumab, trastuzumab, and anti-c-Met antibodies.

44. The method of claim 1, wherein said at least one second agent is chosen from kinase-targeting agents.

45. The method of claim 1, wherein said at least one second agent is chosen from kinase inhibitors.

46. The method of claim 1, wherein said at least one second agent is chosen from tyrosine kinase inhibitors.

47. The method of claim 1, wherein said at least one second agent is chosen from erlotinib, sunitinib, lapatinib, sorafenib, vandetanib, axitinib, bosutinib, cedivanib, dasatinib, gefitinib, imatinib, lestaurtinib, and ARQ197.

48. The method of claim 1, wherein said at least one second agent is chosen from gefitinib, ZD6474, EMD-72000, pariitumab, ICR-62, CI-1033, lapatinib, AEE788, EKB-569, EXEL 7647/EXEL 0999, erlotinib, imatinib, sorafinib, sunitinib, dasatinib, vandetinib, temsirolimus, PTK787, pazopanib, AZD2171, everolimus, seliciclib, AMG 706, axitinib, PD0325901, PKC-412, CEP701, XL880, bosutinib, BIBF1120, BIBF1120, nilotinib, AZD6244, HKI-272, MS-275, BI2536, GX15-070, AZD0530, enzastaurin, MLN-518, and ARQ197.

49. The method of claim 1, wherein said at least one second agent is chosen from erlotinib, lapatinib, and gefitinib.

50. The method of claim 1, wherein said at least one second agent is chosen from angiogenesis inhibitors.

51. The method of claim 1, wherein said at least one second agent is chosen from CM101, IFN-α, IL-12, platelet factor-4, suramin, SU5416, thrombospondin, VEGFR antagonists, angiostatic steroids plus heparin, Cartilage-Derived Angiogenesis Inhibitory Factor, matrix metalloproteinase inhibitors, batimastat, marimastat, angiostatin, endostatin, 2-methoxyestradiol, tecogalan, thrombospondin, αVβ3 inhibitors, linomide, and ADH-1.

52. The method of claim 1, wherein said at least one second agent is chosen from DNA-damaging agents.

53. The method of claim 1, wherein said at least one second agent is chosen from alkylating agents, topoisomerase inhibitors, and DNA intercalators.

54. The method of claim 1, wherein said at least one second agent is chosen from alkylating agents.

55. The method of claim 1, wherein said at least one second agent is chosen from chlorambucil, cyclophosphamide, ifosfamide, mechlorethamine, melphalan, uracil mustard, thiotepa, busulfan, carmustine, lomustine, streptozocin, carboplatin, cisplatin, satraplatin, oxaliplatin, altretamine, ET-743, XL119, dacarbazine, chlormethine, bendamustine, trofosfamide, uramustine, fotemustine, nimustine, prednimustine, ranimustine, semustine, nedaplatin, triplatin tetranitrate, mannosulfan, treosulfan, temozolomide, carboquone, triaziquone, triethylenemelamine, and procarbazin.

56. The method of claim 1, wherein said at least one second agent is chosen from topoisomerase inhibitors.

57. The method of claim 1, wherein said at least one second agent is chosen from doxorubicin, daunorubicin, epirubicin, idarubicin, anthracenedione, mitoxantrone, mitomycin C, bleomycin, dactinomycin, plicatomycin, irinotecan, camptothecin, rubitecan, belotecan, etoposide, teniposide, and topotecan.

58. The method of claim 1, wherein said at least one second agent is chosen from DNA intercalators.

59. The method of claim 1, wherein said at least one second agent is chosen from proflavine, doxorubicin, daunorubicin, dactinomycin, and thalidomide.

60. The method of claim 1, wherein said at least one second agent is chosen from antimitotic agents.

61. The method of claim 1, wherein said at least one second agent is chosen from paclitaxel, taxol, docetaxel, BMS-275183, xyotax, tocosal, vinorlebine, vincristine, vinblastine, vindesine, vinzolidine, etoposide, teniposide, ixabepilone, larotaxel, ortataxel, tesetaxel, and ispinesib.

62. The method of claim 1, wherein said at least one second agent is chosen from antimetabolite agents.

63. The method of claim 1, wherein said at least one second agent is chosen from fluorouracil, floxuridine, methotrexate, xeloda, arranon, leucovorin, hydroxyurea, thioguanine, mercaptopurine, cytarabine, pentostatin, fludarabine phosphate, cladribine, asparaginase, gemcitabine, pemetrexed, bortezomib, aminopterin, raltitrexed, clofarabine, enocitabine, sapacitabine, and azacitidine.

64. The method of claim 1, wherein said at least one second agent is chosen from fluorouracil, methotrexate, capecitabine, leucovorin, gemcitabine, pemetrexed, and bortezomib.

65. The method of claim 1, wherein said at least one second agent is chosen from carboplatin, doxorubicin, gemcitabine, docetaxel, and etoposide.

66. The method of claim 1, wherein said at least one second agent is chosen from doxorubicin, irinotecan, and etoposide.

67. The method of claim 1, wherein said at least one second agent is chosen from carboplatin, cisplatin, satraplatin, oxaliplatin, nedaplatin, triplatin tetranitrate, temozolomide, or procarbazin, or any combination thereof.

68. The method of claim 1, wherein the second agent is chosen from paclitaxel, taxol, docetaxel, xyotax, tocosal, vinorlebine, vincristine, vinblastine, vindesine, vinzolidine, teniposide, ixabepilone, larotaxel, ortataxel, and tesetaxel.

69. The method of claim 1, wherein said at least one second agent is chosen from paclitaxel, taxol, docetaxel, xyotax, larotaxel, ortataxel, and tesetaxel.

70. The method of claim 1, wherein said at least one second agent is paclitaxel.

71. The method of claim 1, wherein said at least one second agent is temozolomide.

72. The method of claim 1, wherein said at least one second agent is doxorubicin.

73. The method of claim 1, comprising administering said composition comprising a therapeutically effective amount of at least one first agent and said composition comprising a therapeutically effective amount of at least one second agent to a human subject with cancer, wherein said cancer is head and neck cancer, brain cancer, breast cancer, lung cancer, liver cancer, pancreatic cancer, ovarian cancer, cervical cancer, uterine cancer, gastrointestinal cancer, kidney cancer, bladder cancer, vulval cancer, cancer of the peritoneum, prostate cancer, thyroid cancer, sarcomas, squamous cell cancer, melanoma, leukemia, lymphoma, or myeloma.

74. The method of claim 1, wherein said composition comprising a therapeutically effective amount of at least one first agent is chosen from compositions consisting of at least one first agent.

75. The method of claim 1, wherein said composition comprising a therapeutically effective amount of at least one first agent further comprises at least one pharmaceutically-acceptable excipient, carrier, or diluent.

76. The method of claim 75, where said at least one pharmaceutically-acceptable excipient, carrier, or diluent is chosen from Gelucire.

77. The method of claim 1, wherein said composition comprising a therapeutically effective amount of at least one second agent is chosen from compositions consisting of at least one second agent.

78. The method of claim 1, wherein said composition comprising a therapeutically effective amount of at least one second agent further comprises at least one pharmaceutically-acceptable excipient, carrier, or diluent.

79. The method of claim 78, where said at least one pharmaceutically-acceptable excipient, carrier, or diluent is chosen from Gelucire.

80. The method of claim 1, wherein said composition comprising a therapeutically effective amount of at least one first agent is formulated for oral administration.

81. The method of claim 1, wherein said composition comprising a therapeutically effective amount of at least one second agent is formulated for oral administration.

82. A method for treating cancer in a human subject in need thereof comprising administering to said subject
a composition comprising a therapeutically effective amount of at least one first agent chosen from 2-acetylnaphtho[2,3-b]furan-4,9-dione and pharmaceutically acceptable solvates thereof,
wherein said 2-acetylnaphtho[2,3-b]furan-4,9-dione is synthetic and
a composition comprising a therapeutically effective amount of at least one second agent chosen from bevacizumab, bortezomib, capecitabine, cetuximab, fluorouracil, imatinib, irinotecan, leucovorin, oxaliplatin, panitumumab, pemetrexed, temozolomide, cisplatin, paclitaxel, erlotinib, sunitinib, lapatinib, sorafenib, carboplatin, doxorubicin, docetaxel, gemcitabine, and etoposide,
wherein said cancer is head and neck cancer, brain cancer, breast cancer, lung cancer, liver cancer, pancreatic cancer, ovarian cancer, cervical cancer, uterine cancer, gastrointestinal cancer, kidney cancer, bladder cancer, vulval cancer, cancer of the peritoneum, prostate cancer, thyroid cancer, sarcoma, squamous cell cancer, melanoma, leukemia, lymphoma, or myeloma, wherein said cancer expresses activated STAT3.

83. The method of claim 82, wherein the cancer is metastatic, refractory to chemotherapy or radiotherapy, resistant to chemotherapy, or has relapsed.

84. A method for treating cancer in a human subject in need thereof comprising administering to said subject
a composition comprising a therapeutically effective amount of at least one first agent chosen from 2-acetylnaphtho[2,3-b]furan-4,9-dione and pharmaceutically acceptable solvates thereof,
wherein said 2-acetylnaphtho[2,3-b]furan-4,9-dione is synthetic and
a composition comprising a therapeutically effective amount of at least one second agent chosen from carboplatin, etoposide, doxorubicin, docetaxel, and gemcitabine,
wherein said cancer is head and neck cancer, brain cancer, breast cancer, lung cancer, liver cancer, pancreatic cancer, ovarian cancer, cervical cancer, uterine cancer, gastrointestinal cancer, kidney cancer, bladder cancer, vulval cancer, cancer of the peritoneum, prostate cancer, thyroid cancer, sarcoma, squamous cell cancer, melanoma, leukemia, lymphoma, or myeloma, wherein said cancer expresses activated STAT3.

85. The method of claim 84, wherein the cancer is metastatic, refractory to chemotherapy or radiotherapy, resistant to chemotherapy, or has relapsed.

86. A method for treating cancer in a human subject in need thereof comprising administering to said subject
a composition comprising a therapeutically effective amount of at least one first agent chosen from 2-acetylnaphtho[2,3-b]furan-4,9-dione and pharmaceutically acceptable solvates thereof,
wherein said 2-acetylnaphtho[2,3-b]furan-4,9-dione is synthetic and
a composition comprising a therapeutically effective amount of paclitaxel,
wherein said cancer is head and neck cancer, brain cancer, breast cancer, lung cancer, liver cancer, pancreatic cancer, ovarian cancer, uterine cancer, cervical cancer, gastrointestinal cancer, kidney cancer, bladder cancer, vulval cancer, cancer of the peritoneum, prostate cancer, thyroid cancer, sarcoma, squamous cell cancer, melanoma, leukemia, lymphoma, or myeloma, wherein said cancer expresses activated STAT3.

87. The method of claim 86, wherein said cancer is ovarian cancer, breast cancer, lung cancer, melanoma, gastrointestinal cancer, cervical cancer.

88. The method of claim 86, wherein said cancer is gastrointestinal cancer.

89. The method of claim 88, wherein said gastrointestinal cancer is esophageal cancer or gastroesophageal junction cancer.

90. The method of claim 88, wherein said cancer is colorectal cancer.

91. The method of claim 86, wherein the cancer is metastatic, refractory to chemotherapy or radiotherapy, resistant to chemotherapy, or has relapsed.

* * * * *

UNITED STATES PATENT AND TRADEMARK OFFICE
CERTIFICATE OF CORRECTION

| | | |
|---|---|---|
| PATENT NO. | : 9,732,055 B2 | |
| APPLICATION NO. | : 12/677516 | |
| DATED | : August 15, 2017 | |
| INVENTOR(S) | : Chiang Jia Li et al. | |

It is certified that error appears in the above-identified patent and that said Letters Patent is hereby corrected as shown below:

In the Specification

Column 1, Line 26, "fraction of the entire tumor mass are responsible" should read --fraction of the entire tumor mass is responsible--.

Column 2, Line 63, "hematopoetic" should read --hematopoietic--.

Column 3, Line 10, "have accounted" should read --has accounted--.

Column 3, Line 49, "have ever been" should read --has ever been--.

Column 4, Line 41, "autoimmtme" should read --autoimmune--.

Column 4, Line 44, "ischernia" should read --ischemia--.

Column 4, Line 45, "sclerosis, Cancers" should read --sclerosis. Cancers--.

Column 6, Lines 17-18, "2-(1-hydroxyethyl)naphtho[2,3-b]furan-4,9-dione," should read --2-(1-hydroxyethyl)-naphtho[2,3-b]furan-4,9-dione,--.

Column 7, Line 34, "the singular form" should read --the singular forms--.

Column 7, Line 35, "the context clearly dictate" should read --the context clearly dictates--.

Column 8, Line 5, "hut are not" should read --but are not--.

Column 8, Lines 19-20, "mass of tissue that result" should read --mass of tissue that results--.

Column 8, Line 57, "the term" should read --the terms--.

Signed and Sealed this
Nineteenth Day of December, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,732,055 B2

Column 8, Line 62, "may refers" should read --may refer--.

Column 11, Table 1, under the "DISEASES" column, Line 16, "Reumatoid Arthritis" should read --Rheumatoid Arthritis--.

Column 11, Table 1, under the "DISEASES" column, Line 25, "Polycythernia vera" should read --Polycythemia vera--.

Column 11, Table 1, under the "DISEASES" column, Line 26, "Alzhemer's" should read --Alzheimer's--.

Column 12, Line 66, "getfitinib (irressa), imatinib (gleevac)," should read --getfitinib (ircssa), imatinib (glccvcc),--.

Column 13, Line 3, after "(ABX-EGF),", please insert --ICR-62,--.

Column 16, Lines 26-27, "is targeted agent," should read --is a targeted agent,--.

Column 16, Lines 45-46, "more than one pathway that are implicated" should read --more than one pathway that is implicated--.

Column 16, Lines 57-58, "combination, lower amount is able" should read --combination, a lower amount is able--.

Column 17, Line 3, "pre-combination rate" should read --pre-combination rates--.

Column 17, Line 47, "Panel," should read --Panc1,--.

Column 17, Line 61, "5 µg/mL The labeled cells" should read --5 µg/mL. The labeled cells--.

Column 17, Line 65, "passed a through 40 µm" should read --passed through a 40 µm--.

Column 18, Line 9, "have accounted" should read --has accounted--.

Column 18, Line 32, "Biosicences," should read --Biosciences,--.

Column 18, Lines 39-40, "capacity of cell population if the ability" should read --capacity of a cell population is the ability--.

Column 18, Line 46, "spheres formation." should read --sphere formation.--.

Column 18, Line 67 to Column 19, Line 1, "according to manufactures directions" should read --according to the manufacturer's directions--.

Column 19, Line 1, "Armexin-V" should read --Annexin-V--.

CERTIFICATE OF CORRECTION (continued)
U.S. Pat. No. 9,732,055 B2

Column 20, Line 38, "cocktail siRNAs" should read --cocktail of siRNAs--.

Column 20, Line 67 to Column 21, Line 1, "harvested or analysis" should read --harvested for analysis--.

Column 21, Lines 44-45, "immunofluorence" should read --immunofluorescence--.

Column 21, Lines 58-59, "Stat3 are" should read --Stat3 is--.

Column 22, Line 6, "Hoeschst" should read --Hoechst--.

Column 22, Line 22, "sphereogenesis," should read --spherogenesis,--.

Column 23, Line 52, "stein cell" should read --stem cell--.

Column 26, Table 4, in the tenth line under the "X (% Inhibition)" column of the "7 day colony formation PACA2 cells" section of the table, "36 [33 µM]" should read --36 [33 nM]--.

Column 26, Table 4, in the first line under the "X (% Inhibition)" column of the "72 hour MTT HepG2 cells" section of the table, "23 [12.5 µM]" should read --23 [12.5 nM]--.

Column 27, Line 12, "pancreatic cancer" should read --pancreatic cancer.--.

Column 29, Line 29, "Brain Res Brain Res Rev," should read --Brain Res Rev,--.

Column 29, Line 67, "Br Cancer," should read --Br J Cancer,--.

In the Claims

Claim 1, Column 33, Line 28, "synthetic and" should read --synthetic, and--.

Claim 18, Column 34, Line 28, "claim 1," should read --claim 17,--.

Claim 40, Column 35, Line 8, "bevacizurnab," should read --bevacizumab,--.

Claim 48, Column 35, Line 36, "pariitumab," should read --patritumab,--.

Claim 48, Column 35, Line 41, "BIBF1120, BIBF1120, nilotinib," should read --BIBF1120, nilotinib,--.

Claim 82, Column 37, Line 42, "synthetic and" should read --synthetic, and--.

Claim 84, Column 38, Line 11, "synthetic and" should read --synthetic, and--.

Claim 86, Column 38, Line 34, "synthetic and" should read --synthetic, and--.

SEQUENCE LISTING

```
<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Oligonucleotide sequence
<220> FEATURE:
<221> NAME/KEY: misc_feature
<222> LOCATION: (1)..(1)
<223> OTHER INFORMATION: 5'-biotin

<400> SEQUENCE: 1
gatccttctg ggaattccta gatc                                              24

<210> SEQ ID NO 2
<211> LENGTH: 24
<212> TYPE: DNA
<213> ORGANISM: Artificial Sequence
<220> FEATURE:
<223> OTHER INFORMATION: Oligonucleotide sequence

<400> SEQUENCE: 2
ggatctagaa tcagctacag cagc                                              24

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide sequence

<400> SEQUENCE: 3
tcctctagag ggcaatctcc attg                                              24

<210> SEQ ID NO 4
<211> LENGTH: 22
<212> TYPE: DNA
<213> ORGANISM: Artificial Sequence
```

```
<220> FEATURE:
<223> OTHER INFORMATION: Oligonucleotide sequence

<400> SEQUENCE: 4
ccctctagat ggttcctgga ac                                                  22

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 5
gctctagaaa ccccttttg g                                                    21
```